(12) United States Patent
Bonutti et al.

(10) Patent No.: US 8,591,441 B2
(45) Date of Patent: Nov. 26, 2013

(54) SHOULDER ORTHOSIS INCLUDING FLEXION/EXTENSION DEVICE

(76) Inventors: Peter M. Bonutti, Effingham, IL (US);
Boris P. Bonutti, Effingham, IL (US);
Glen A. Phillips, Effingham, IL (US);
Kevin R. Ruholl, Teutopolis, IL (US);
Clayton D. Britton, Newton, IL (US)

( * ) Notice: Subject to any disclaimer, the term of this patent is extended or adjusted under 35 U.S.C. 154(b) by 312 days.

(21) Appl. No.: 12/910,682

(22) Filed: Oct. 22, 2010

(65) Prior Publication Data

US 2012/0101419 A1    Apr. 26, 2012

(51) Int. Cl.
*A61F 5/00*    (2006.01)

(52) U.S. Cl.
USPC ............................................. 602/16; 602/20

(58) Field of Classification Search
USPC ............. 602/4–5, 19–20, 16; 128/877–879, 8
See application file for complete search history.

(56) References Cited

U.S. PATENT DOCUMENTS

| | | | |
|---|---|---|---|
| 2,191,283 A | 2/1940 | Longfellow | |
| 2,310,566 A * | 2/1943 | Anderson | 602/19 |
| 4,417,569 A * | 11/1983 | Brudny | 602/20 |
| 5,407,420 A | 4/1995 | Bastyr et al. | |
| 5,417,643 A * | 5/1995 | Taylor | 601/33 |
| 5,538,499 A | 7/1996 | Schwenn et al. | |
| 5,558,624 A * | 9/1996 | Hepburn et al. | 601/33 |
| 5,645,521 A | 7/1997 | Hepburn et al. | |
| 5,665,058 A * | 9/1997 | Young | 602/20 |
| 5,848,979 A | 12/1998 | Bonutti et al. | |
| 6,007,500 A * | 12/1999 | Quintinskie, Jr. | 601/5 |
| 6,113,562 A | 9/2000 | Bonutti et al. | |
| 6,533,741 B1 * | 3/2003 | Lee et al. | 602/20 |
| 7,547,289 B2 * | 6/2009 | Branch | 601/5 |
| 2004/0153010 A1 | 8/2004 | Bonutti et al. | |
| 2009/0264799 A1 | 10/2009 | Bonutti et al. | |

OTHER PUBLICATIONS

Joint Active Systems, Shoulder: Body Cuff Model Fitting Instructions, Mar. 2010, 2 pages.

* cited by examiner

*Primary Examiner* — Michael A. Brown
(74) *Attorney, Agent, or Firm* — Armstrong Teasdale LLP

(57) ABSTRACT

A shoulder orthosis includes a shoulder therapy device adapted to provide treatment to a shoulder joint of a person, and a flexion/extension device. The flexion/extension device positions the shoulder joint in at least one of greater than 0 degrees of flexion and greater than 0 degrees of extension concurrently with the shoulder therapy device providing the treatment to the shoulder joint. In one example, the shoulder therapy device may be an abduction/adduction device and/or an internal/external rotation device.

24 Claims, 23 Drawing Sheets

SHOULDER ORTHOSIS INCLUDING FLEXION/EXTENSION DEVICE

FIELD OF THE DISCLOSURE

The present disclosure relates generally to a shoulder orthosis, and more particularly, to a shoulder orthosis which includes a flexion/extension device.

BACKGROUND OF THE DISCLOSURE

In general, a range-of-motion of a joint in the human body is the distance (e.g., linear or rotational) the joint can move in a certain direction. For example, movements of the shoulder joint (i.e., the glenohumeral joint) include flexion, extension, abduction, adduction, and internal and external rotation. Flexion of the shoulder joint involves rotational movement of the upper arm anteriorly, and extension involves rotational movement of the upper arm posteriorly. Abduction of the shoulder joint involves rotational movement of the upper arm laterally away from the midline of the body (e.g., upward), and adduction involves rotational movement of the upper arm medially toward the midline (e.g., downward). Internal (e.g., medial) rotation of the shoulder joint involves rotation of the upper arm about its longitudinal axis, toward the midline of the body, and external (e.g., lateral) rotation of the shoulder joint involves rotation of the upper arm about its longitudinal axis away from the midline. Internal (e.g., medial) rotation may involve inferior (e.g., downward) rotation of the forearm when the upper arm is abducted and the elbow is flexed 90 degrees, and external (e.g., lateral) rotation may involve superior (e.g., upward) rotation of the forearm when the upper arm is abducted and the elbow is flexed 90 degrees. Combinations of these shoulder joint movements are also possible, including transverse (e.g., horizontal) adduction (e.g., combining flexion and adduction), transverse (e.g., horizontal) abduction (e.g., combining extension and abduction), and circumduction (e.g., combining all directions of movement).

When a joint is injured, either by trauma or by surgery, scar tissue can form or tissue can contract and consequently limit the range-of-motion of the joint. For example, adhesions can form between tissues and the muscle can contract itself with permanent muscle contracture or tissue hypertrophy such as capsular tissue or skin tissue. Lost or limited range-of-motion may also result from trauma, such as excessive temperature (e.g., thermal or chemical burns), or surgical trauma, so that tissue planes which normally glide across each other may become adhered together, markedly restricting motion. The adhered tissues may result from chemical bonds, tissue hypertrophy, proteins such as Actin or Myosin in the tissue, or simply from bleeding and immobilization. It is often possible to mediate, and possibly even correct this condition by use of a range-of-motion (ROM) orthosis, but the longer the period of stiffness or loss of motion the greater the time interval and the force required to regain lost range-of-motion. Therefore, it is beneficial to treat the tissue or joint as early as possible. For example, a ROM orthosis may be applied immediately after surgery or as soon as the stiffness problem is diagnosed. ROM orthoses may also be used for tissue transport, bone lengthening, stretching of skin or other tissue, tissue fascia, and the like.

SUMMARY

In an aspect, a shoulder orthosis generally comprises a shoulder therapy device adapted to provide treatment to a shoulder joint of a person, and a flexion/extension device. The flexion/extension device is configured to position the shoulder joint in at least one of greater than 0 degrees of flexion and greater than 0 degrees of extension concurrently with the shoulder therapy device providing the treatment to the shoulder joint.

In another aspect, a method of treating a shoulder joint of a person using a shoulder orthosis that includes a flexion/extension device and a shoulder therapy device is provided. The method generally comprises operatively securing at least a portion of an arm associated with shoulder joint to the shoulder orthosis. The shoulder joint is positioned using the flexion/extension device in one of greater than 0 degrees of flexion and greater than 0 degrees of extension. The shoulder therapy device is operated to facilitate movement of the shoulder joint after positioning the shoulder joint using the flexion/extension device.

In another aspect, a shoulder orthosis generally comprises a torso securing device configured for removable securement to a torso of a person. An internal/external rotation device is adapted to facilitate at least one of internal rotation and external rotation of a shoulder joint of the person. A flexion/extension device operatively connects the internal/external rotation device to the torso securing device. The flexion/extension device is configured to position the shoulder joint in greater than 0 degrees of flexion when the torso securing device is secured to the torso and as the internal/external rotation device is facilitating at least one of internal rotation and external rotation of the shoulder joint.

BRIEF DESCRIPTION OF THE DRAWINGS

Corresponding reference characters indicate corresponding parts throughout the drawings.

DETAILED DESCRIPTION OF THE DRAWINGS

Figure 1A:
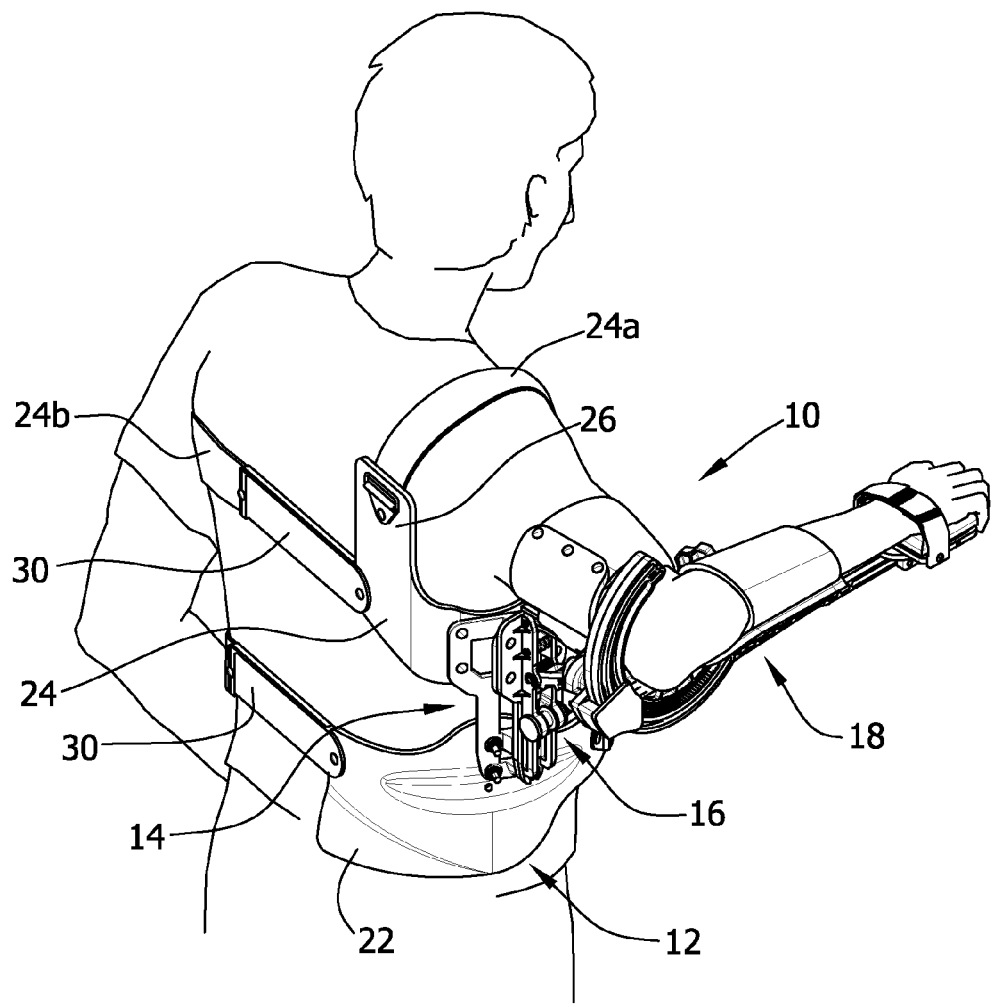
FIG. 1A is a rear perspective of a shoulder orthosis secured to a torso and an arm of a person.
Figure 1B:
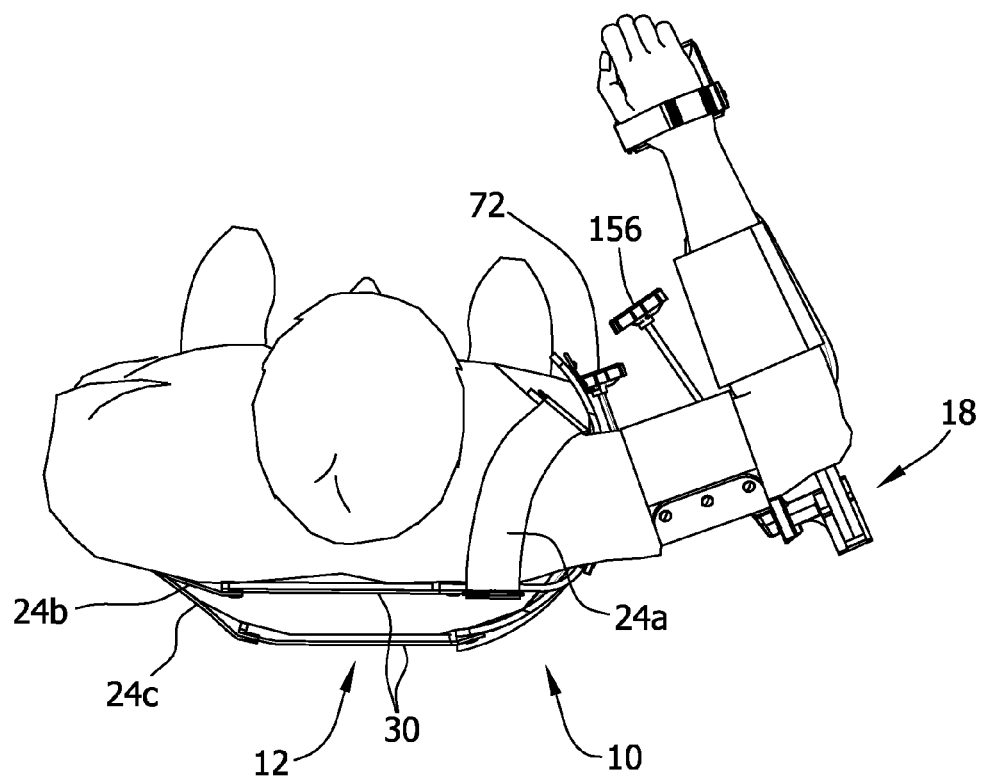
FIG. 1B is a top plan of FIG. 1A.
Figure 2:
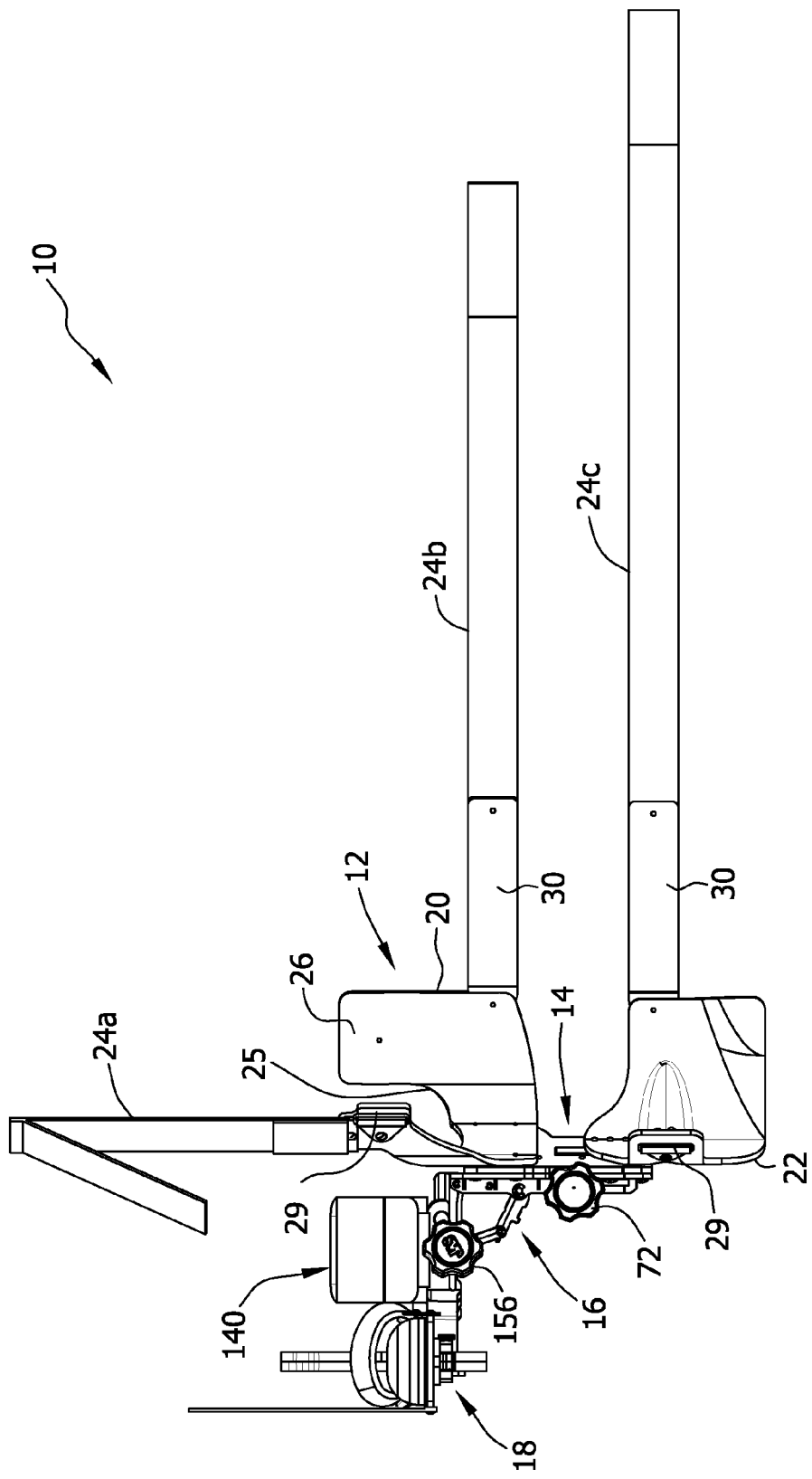
FIG. 2 is front elevation of the shoulder orthosis.
Figure 3:
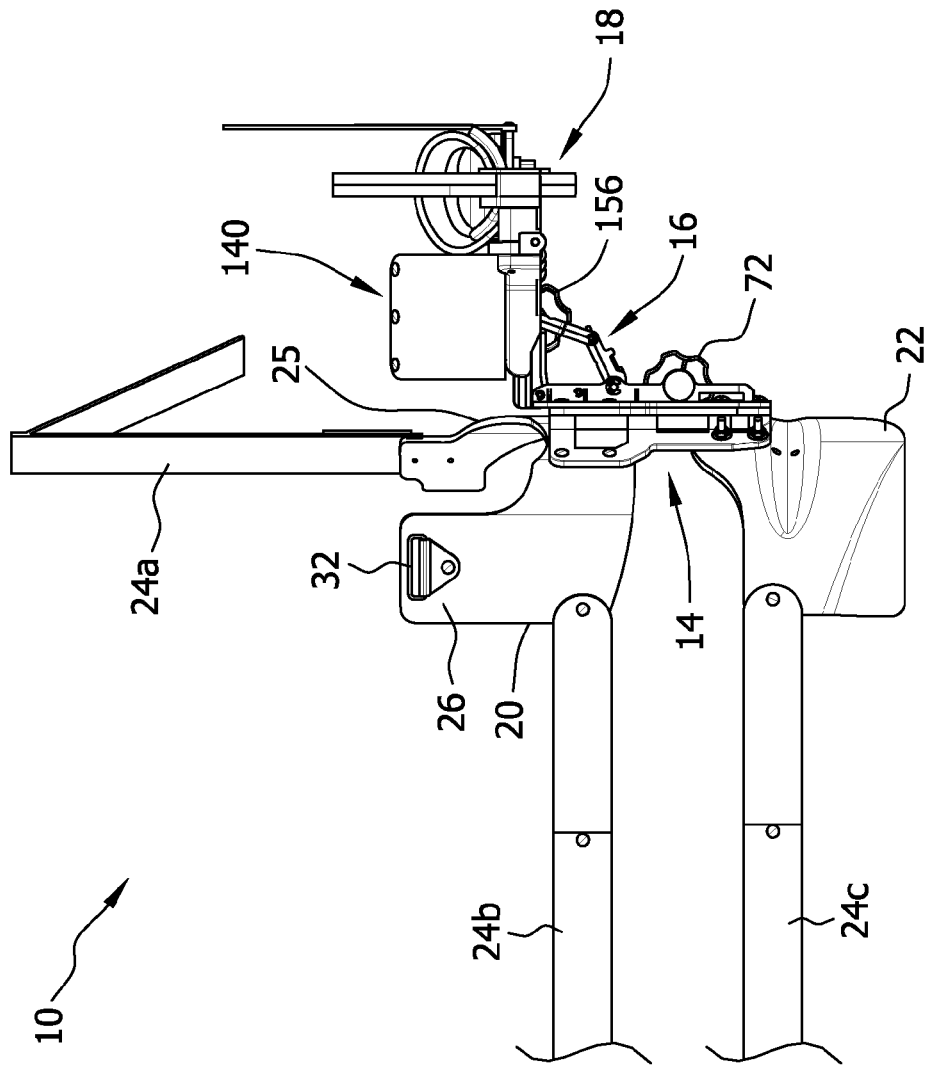
FIG. 3 is a rear elevation of the shoulder orthosis.
Figure 4:
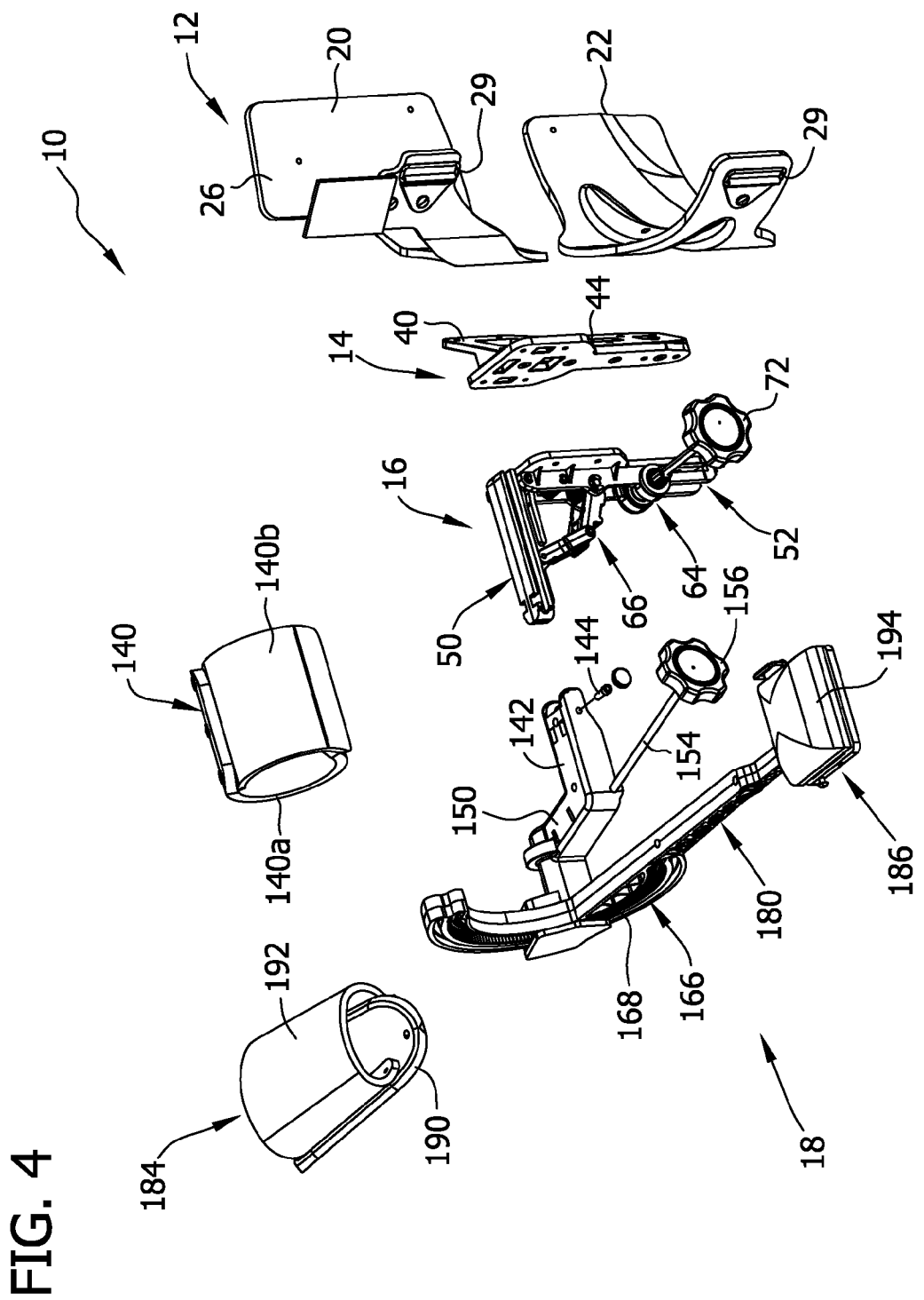
FIG. 4 is an exploded view of the shoulder orthosis illustrating a torso securing device, a flexion/extension device, an abduction/adduction device, and an internal/external rotation device of the orthosis, with straps on the torso securing device being removed for illustrative purposes.
Figure 5:
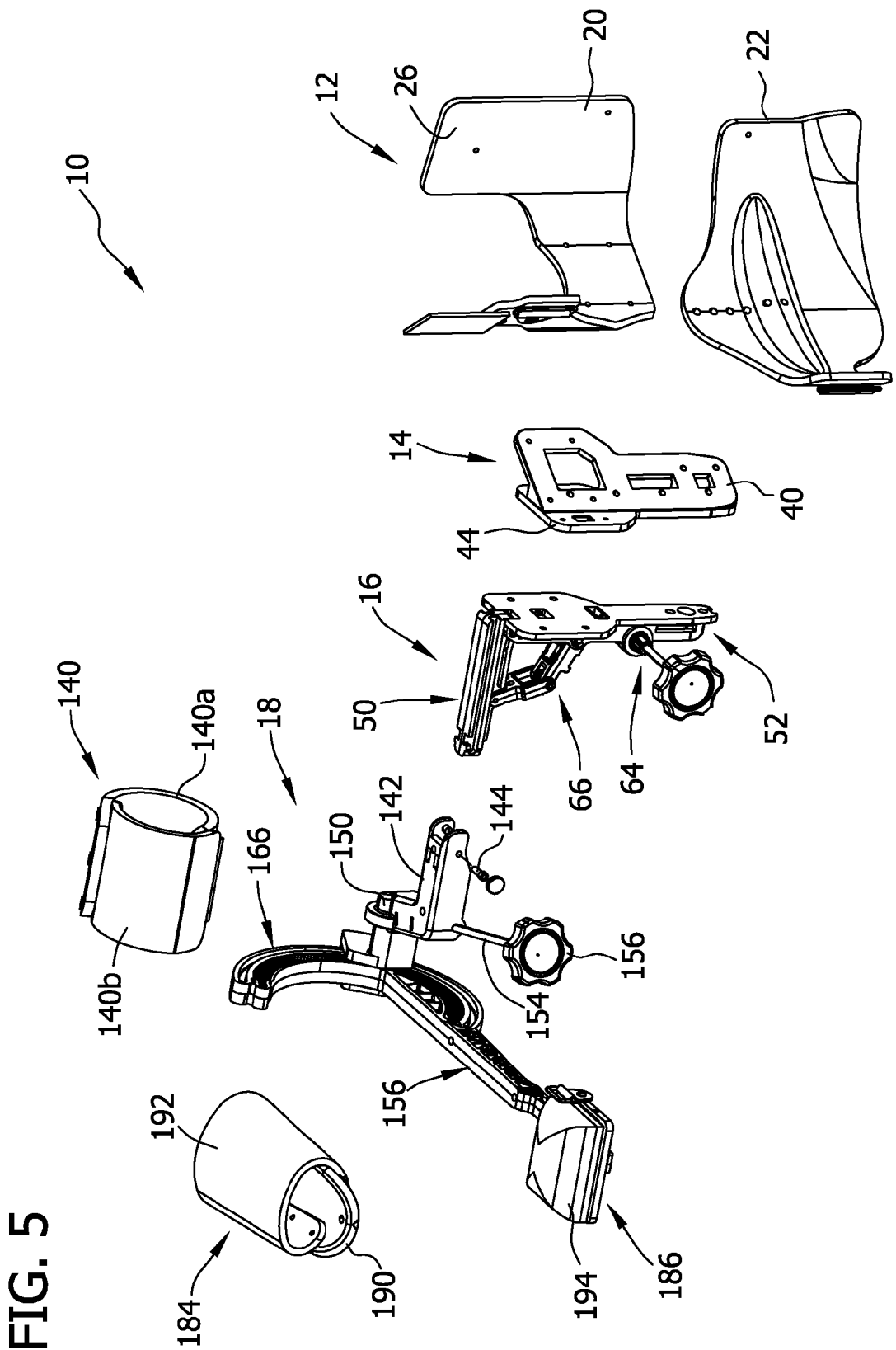
FIG. 5 is an exploded view of the shoulder orthosis similar to FIG. 4, except taken from a different viewpoint for illustrative purposes.

Referring now to the drawings, and in particular to FIGS. 1A and 1B, a shoulder orthosis for use in treating a shoulder joint (i.e., glenohumeral joint) of a person is generally indicated at 10. In general, the illustrated shoulder orthosis 10 provides passive range-of-motion (ROM) exercise of the shoulder, although it is understood that the shoulder orthosis may be configured to facilitate active assisted range-of-motion exercise or the orthosis may be configured to apply static support and/or substantially immobilize the shoulder joint. The illustrated shoulder orthosis 10 is configured for treating a right shoulder of a person, however, the principles disclosed herein apply equally to a shoulder orthosis configured for treating a left shoulder of the user.

Referring to FIG. 1A through FIG. 5, the shoulder orthosis 10 comprises a torso securing device, generally indicated at 12, for removably securing the shoulder orthosis 10 to a torso of a person. The shoulder orthosis 10 also includes a flexion/extension device, generally indicated at 14, for selectively facilitating flexion and/or extension of the shoulder joint; an abduction/adduction device, generally indicated at 16, for selectively facilitating abduction and/or adduction of the shoulder joint; and an internal/external rotation device, generally indicated at 18, for selectively facilitating internal rotation and/or external rotation of the shoulder joint. In the illustrated embodiment, the internal/external rotation device 18 is operatively secured to the abduction/adduction device 16, and the flexion/extension device 14 operatively connects the abduction/adduction device, and in turn the internal/external rotation device, to the torso securing device 12. Other configurations are possible and may be within the scope of the present disclosure.

Broadly, the abduction/adduction device and the internal/external rotation device are "shoulder therapy devices", meaning that for the devices facilitate moving and/or positioning the shoulder joint in one or more of internal rotation, external rotation, abduction, and adduction. As explained below, the illustrated abduction/adduction device positions the shoulder joint in a selected degree of abduction, and the illustrated internal/external device positions the shoulder joint in a selected degree of each of internal and external rotation. It is understood that the orthosis may include one or more different therapy devices, in combination with or in place of the abduction/adduction device and the internal/external rotation device, for combining the movements of the abduction/adduction device and the internal/external rotation device. The orthosis 10 may also include therapy devices for treating other joints in addition to the shoulder joint, such as the elbow joint, the wrist joint, and the radioulnar joint.

Torso Securing Device

Referring to FIG. 1A through FIG. 6, the torso securing device 12 of the shoulder orthosis 10 includes a thoracic support 20, a waist support 22, and adjustable straps 24a, 24b, 24c for securing the thoracic and waist supports to the person. As seen best in FIG. 1A, the thoracic support 20 is configured to engage the right rib cage (i.e., right lateral thorax) of the person and extend anteriorly and posteriorly so as to at least partially wrap around the right rib cage. The thoracic support 20 has an armpit recess 25 for receiving the armpit (i.e., axially) of the person and a scapular portion 26 (a superior and posterior portion of the thoracic support) for engaging the scapula. The waist support 22 is configured to engage the right portion of the waist region of the person and extend anteriorly and posteriorly so as to at least partially wrap around the right waist region. The waist support 22 may engage a lower portion of the right rib cage and the right hip. The thoracic and waist supports 20, 22, respectively, may each include a semi-rigid outer shell (as illustrated) that provides some resilient flexibility for fitting the supports on torsos of various sizes. A soft and compressible inner liner (not shown) may be secured to the interior of the outer shell to provide comfort to the person. In the illustrated embodiment, the thoracic and waist supports 20, 22, respectively, are formed as separate components and secured to one another by the flexion/extension device 14, as explained below. In another embodiment, the supports 20, 22 may be integrally formed as a one-piece component.

As seen best in FIG. 1A through FIG. 3, in the illustrated embodiment, the adjustable straps designated at 24a, 24b are secured to the thoracic support 20, and the adjustable strap 24c is secured to the waist support 22. In general, the adjustable straps 24a, 24b, 24c are adjustable in functioning length and configured to substantially hold the thoracic and waist supports 20, 22 against movement relative to the torso of the person during use of the orthosis 10. The straps designated 24b, 24c are transverse straps that are configured to extend transversely around the rib cage and the waist, respectively, and the strap designated 24a is a shoulder strap that is configured to extend around the clavicle of the right shoulder. The torso securing device 12 may be removably securable to the torso of the person in other ways.

In the illustrated embodiment, the transverse straps 24b, 24c have fixed ends secured to posterior sides of the respective thoracic and waist supports 20, 22 and free end margins that are insertable into and releasably securable around D-rings 29 (FIG. 2) on anterior sides of the respective thoracic and waist supports. The transverse straps 24b, 24c may include hook and loop fasteners (e.g., hook and loop fasteners) for securing the straps to the D-rings 29, or the straps may be releasably fastenable to the D-rings in other ways. The straps 24b, 24c also includes a relatively semi-rigid, padded segment 30 that engages the posterior region (i.e., the back) of the person and provides a level of comfort to the person. The segments 30 also hold the straps 24b, 24c in a position that the patient can readily and easily reach. The straps 24a, 24b, 24c may include additional padding or other soft and/or compressible material to provide comfort. The straps 24b, 24c may be of other configurations without departing from the scope of the present disclosure.

The shoulder strap 24a has a fixed end secured to an anterior side of the thoracic support 20 and a free end margins that are insertable into and releasably securable around a D-ring 32 (FIG. 3) on an posterior side of the thoracic support. The shoulder strap 24*a* may include hook and loop fasteners (e.g., hook and loop fasteners) for securing the straps to the D-ring 32, or the strap may be releasably fastenable to the D-ring in other ways. The shoulder strap 24*a* may include padding or other soft and/or compressible material to provide comfort. The strap 24*a* is also configured in such way that allows the patient to readily reach the strap even after it is fed through the D-ring 32. The strap 24*a* may be of other configurations without departing from the scope of the present disclosure.

It is understood that the torso securing device 12 may be of other configurations without departing from the scope of the present disclosure. For example, the torso securing device may not include the thoracic support 20 or the waist support 22 or any other torso support. In such an embodiment, the torso securing device may include straps that are secured directly to one or more of shoulder therapy devices, such as the abduction/adduction device and the internal/external rotation device, or to the flexion/extension device. Other configurations do not depart from the scope of the present disclosure.

Moreover, the orthosis 10 may be configured for mounting on a stand, such as disclosed in U.S. Patent Application Publication No. 2009/0264799, filed Oct. 22, 2009, the teachings of which relating to the mounting of an orthosis on a stand are herein incorporated by reference. In such an embodiment, the torso securing device 12 of the illustrated embodiment disclosed herein may be omitted or replaced with another type of securing device, without departing from the scope of the present disclosure.

Flexion/Extension Device

As used herein, the term "flexion/extension device" is a device that is configured to move and/or position the shoulder joint in at least one of a selected degree of flexion (which may include transverse adduction when the shoulder joint is in abduction) and a selected degree of extension (which may include transverse abduction when the shoulder joint is in abduction), or only one of a selected degree of flexion and a selected degree of extension. Moreover, the flexion/extension device may be non-adjustable, such that the degree of flexion/extension of the shoulder is fixed (FIGS. 4-6 and 7A), or the flexion/extension device may be selectively adjustable, to allow for selective adjustment of the degree of flexion and/or extension of the shoulder joint (FIGS. 7B through 7F).

Figure 6:
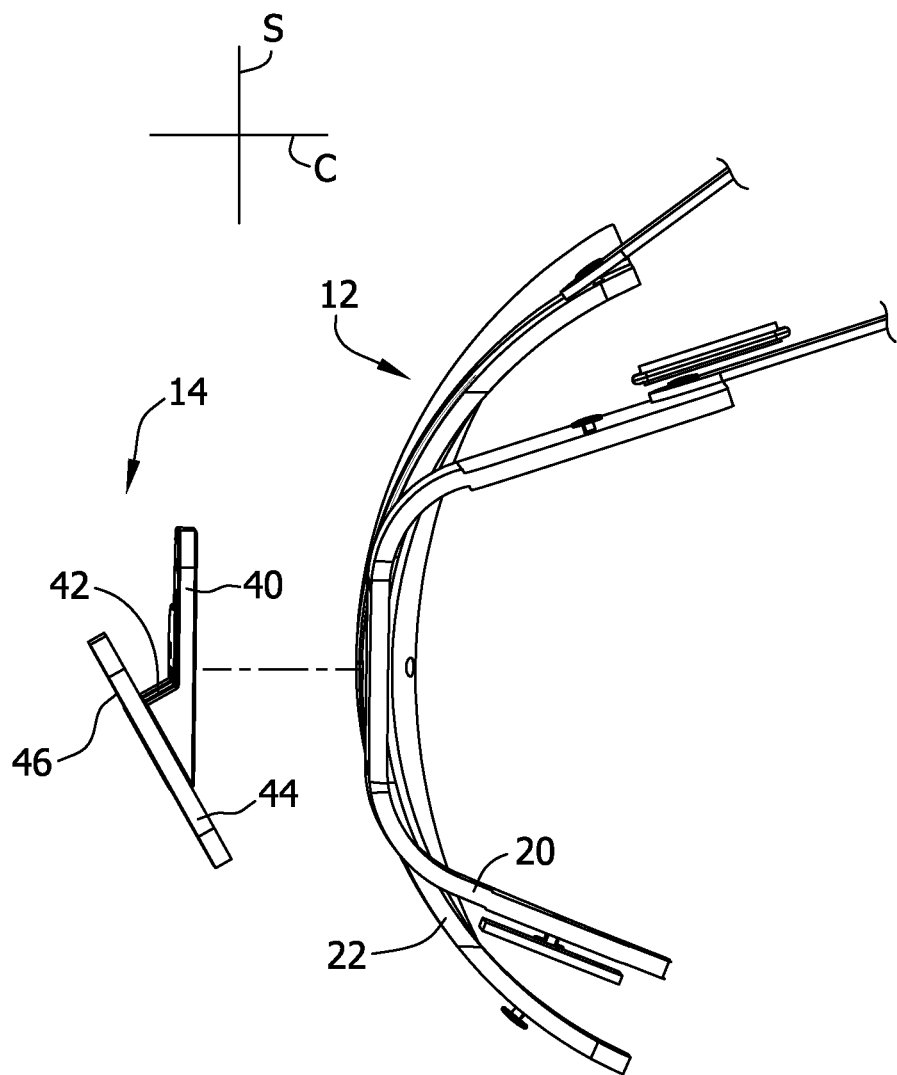
FIG. 6 is an enlarged top plan view of the torso securing device and the flexion/extension device exploded therefrom.

In the illustrated embodiment of FIGS. 4-6 and 7A, the flexion/extension device 14 includes a first load-bearing plate 40 (broadly, a first load-bearing member) fixedly secured to lateral portions of the thoracic and waist supports 20, 22, respectively, and positioned generally immediately below the armpit recess. When the torso securing device 12 is secured to the torso, the load-bearing plate 40 is configured to lie substantially in a sagittal plane S (i.e. any longitudinal plane that passes from the anterior to the posterior of the body, divides the body into right and left portions, and is parallel to the median plane) and intersect the mid-coronal plane C (i.e. any longitudinal plane that is at a right angle of the sagittal plane, which divides the body into anterior and posterior portions) of the person's body, as seen in FIG. 6, for example. The load-bearing plate 40 includes an angular positioning member 42, which may be a separate component or formed integrally with the load-bearing plate. In the illustrated embodiment, a second load-bearing plate 44 (broadly, a load-bearing member) is secured to the angular positioning member 42, such as by threaded fasteners, so that the angular positioning member 42 angular offsets the second-load bearing plate 44 relative to a sagittal plane of the person's body.

As explained in more detail below, the abduction/adduction device 16 is secured to a mounting surface 46 (FIGS. 6 and 7) of the second load-bearing plate 44 such that the flexion/extension device 14 operatively connects the abduction/adduction device and the internal/external rotation device 18 to the torso securing device 12, although it is understood that the flexion/extension device may not operatively connect the abduction/adduction device and the internal/external rotation device 18 to the torso securing device 12 without departing from the scope of the present disclosure. Broadly, the illustrated flexion/extension device functions as a shim, positioned between the torso-securing device 12 and the abduction/adduction device 16, and in turn, the internal/external rotation device, to provide a desired angular offset between the torso-securing device and the respective devices. As explained below, the abduction/adduction device 16 defines an abduction/adduction plane through which the upper arm moves under load of the abduction/adduction device. The illustrated flexion/extension device 14 angularly offsets this abduction/adduction plane relative to a sagittal plane of the person's body to provide flexion of the shoulder when the user's arm is secured to the orthosis.

As seen in FIGS. 1A and 1B, the flexion/extension device 14 of this illustrated embodiment is configured to position the shoulder joint at about 30 degrees of flexion. It is believed that about 30 degrees of flexion of the shoulder joint will generally locate the upper arm, and more specifically, the abduction plane of the shoulder, in a plane that is substantially coplanar with and/or parallel to a scapular plane defined by the scapula. It is also believed that positioning the shoulder joint in flexion coplanar with (e.g., parallel to) the scapular plane when treating the shoulder joint, such as by adduction or abduction and/or internal or external rotation, has certain therapeutic benefits. It is contemplated that in other embodiments, the flexion/extension device 14 may be configured to place the shoulder joint from about 5 degrees to about 90 degrees of flexion, more specifically, about 10 degrees to about 60 degrees flexion, or about 15 degrees to about 45 degrees flexion, or about 20 degrees to about 40 degrees, or about 25 degrees to about 35 degrees. Moreover, the flexion/extension device 14 may be configured to facilitate positioning of the shoulder joint at a selected degree of extension, such as from about 1 degree of extension to about 10 degrees of extension. Broadly, the flexion/extension device 14 is configured to position the shoulder joint at least one of greater than 0 degrees of flexion and greater than 0 degrees of extension. It is understood that the flexion/extension device 14 may have other configurations without departing from the scope of the present disclosure. For example, the flexion/extension device 14 may not include the first load-bearing plate 40 or the second load-bearing plate 44, as illustrated, and may include a component other than the angular positioning member 42 for facilitating flexion and/or extension of the shoulder.

In another embodiment, as seen in the illustrated embodiment of FIGS. 7B through 7F, the flexion/extension device 14' is selectively adjustable to allow for selective adjustment of the degree of flexion and/or extension of the shoulder joint. Selective adjustability of the degree of flexion and/or extension of the shoulder joint provides for greater range-of-motion treatment to the shoulder joint. Moreover, the adjustable flexion/extension device may be used to more properly position the longitudinal axis of the upper arm (more specifically, the abduction/adduction plane of the shoulder joint) coplanar with the scapular plane. Thus, the adjustability of the flexion/extension device may be more beneficial than a fixed flexion/extension device of 30 degree flexion where a person's scapular plane may be angularly offset either greater than or less than 30 degrees relative to a coronal plane, for example.

As seen in FIGS. 7B through 7F, the adjustable flexion/extension device 14' of this embodiment includes first and second load-bearing plates 40', 44', respectively. The second load-bearing plate 44' is coupled to the first load-bearing plate 40' to allow for rotational movement of the second load-bearing plate, and in turn, rotational movement of the abduction/adduction device 16 and the internal/external rotation device 18, about the first load-bearing plate, generally within a plane defined by a transverse plane of the person's body. In particular, the illustrated first load-bearing plate 40' includes upper and lower angular displacement members 42' that are generally in the form of arcuate rails or tracks. The illustrated second load-bearing plate 44' includes cantilevered upper and lower hook members 45' that slidably engage the arcuate tracks 42' to slidably secure the second load-bearing plate 44' to the first load-bearing plate 40'. As can be seen from FIG. 7D, the mounting surface 46' of the second load-bearing plate 44', to which the abduction/adduction device 16 is secured, remains in planes that are substantially tangential to the arcuate tracks as the second load-bearing plate slides along the arcuate tracks 42'. As such, the arcuate tracks 42' provide limited rotational movement of the second load-bearing plate 44' relative to the first load-bearing plate 40', and in turn, the flexion/extension device 14' facilitates selective adjustment of the degree of flexion and/or extension of the shoulder joint. A chamfered anterior edge 43' of the first load-bearing plate 40' provides clearance for the second load-bearing plate 44' when the second load-bearing plate is slid to an anterior position on the first load-bearing plate. In the illustrated embodiment, the axis of rotation of the flexion/extension device 14' is generally aligned vertically (inferior-superior) with the flexion/extension rotation axis of the shoulder joint.

Figure 7A:
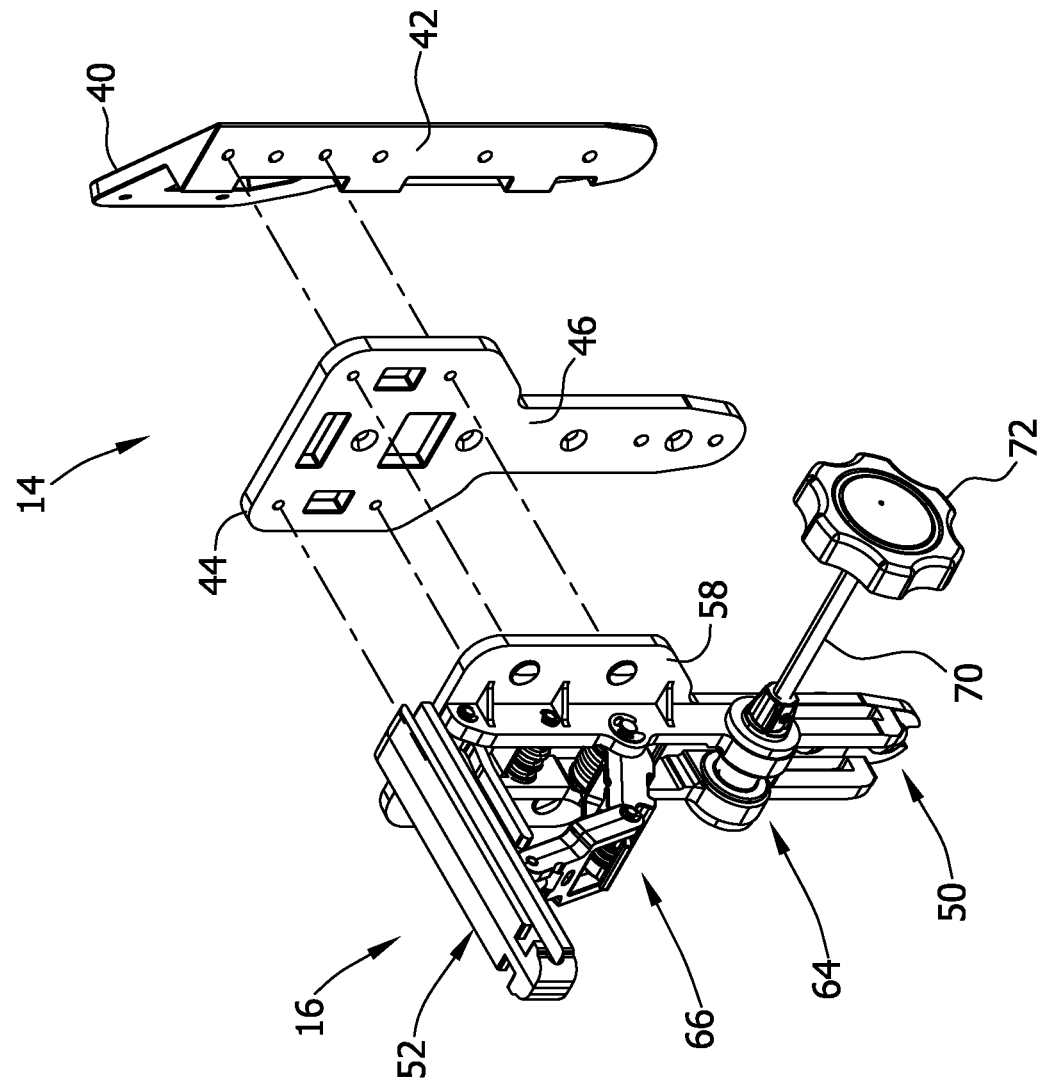
FIG. 7A is an enlarged exploded perspective of the flexion/extension device and the abduction/adduction device, with the flexion/extension device also being exploded into separate component.
Figure 7B:
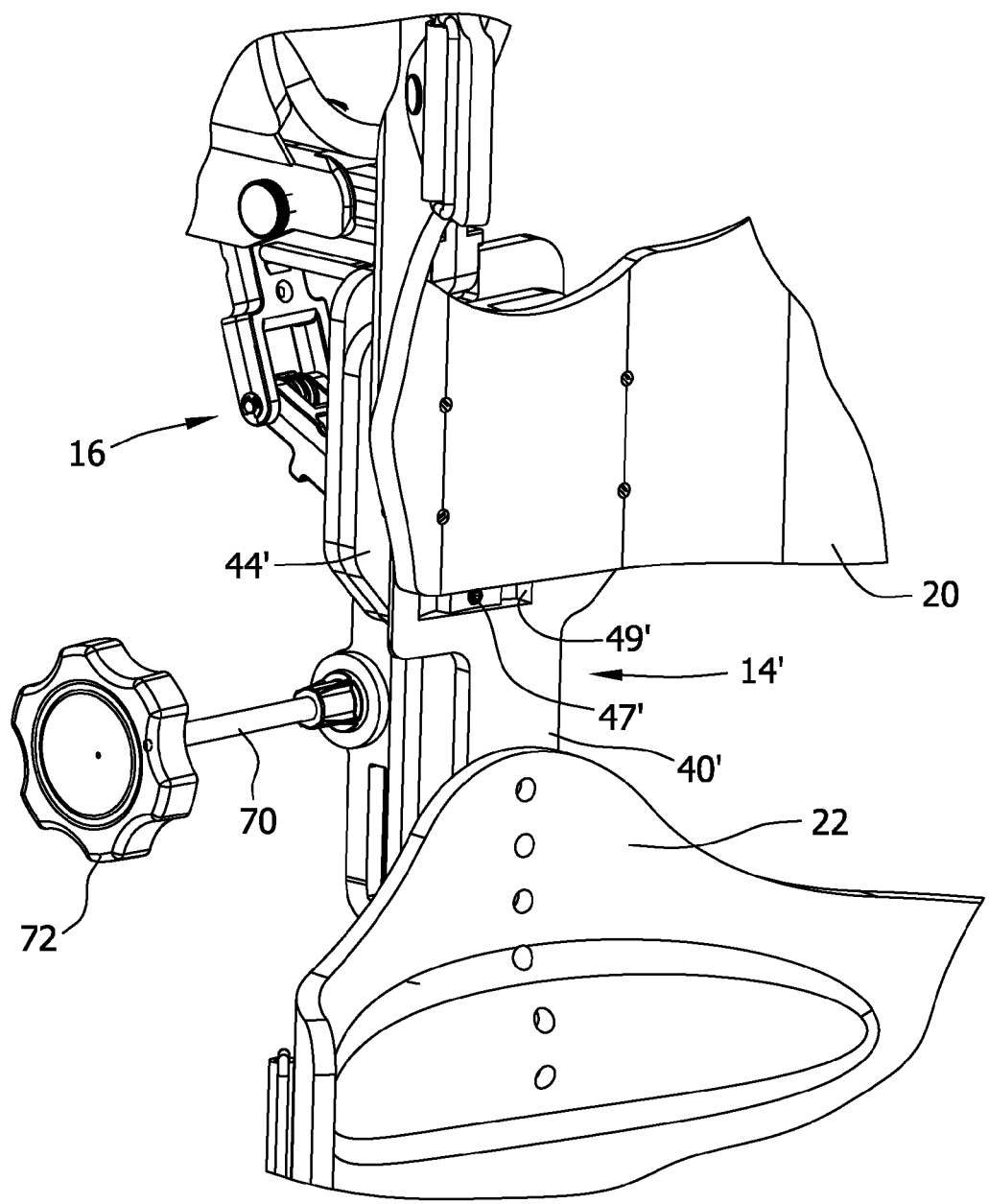
FIG. 7B is a fragmentary perspective of the shoulder orthosis including a second embodiment of the flexion/extension device.
Figure 7C:
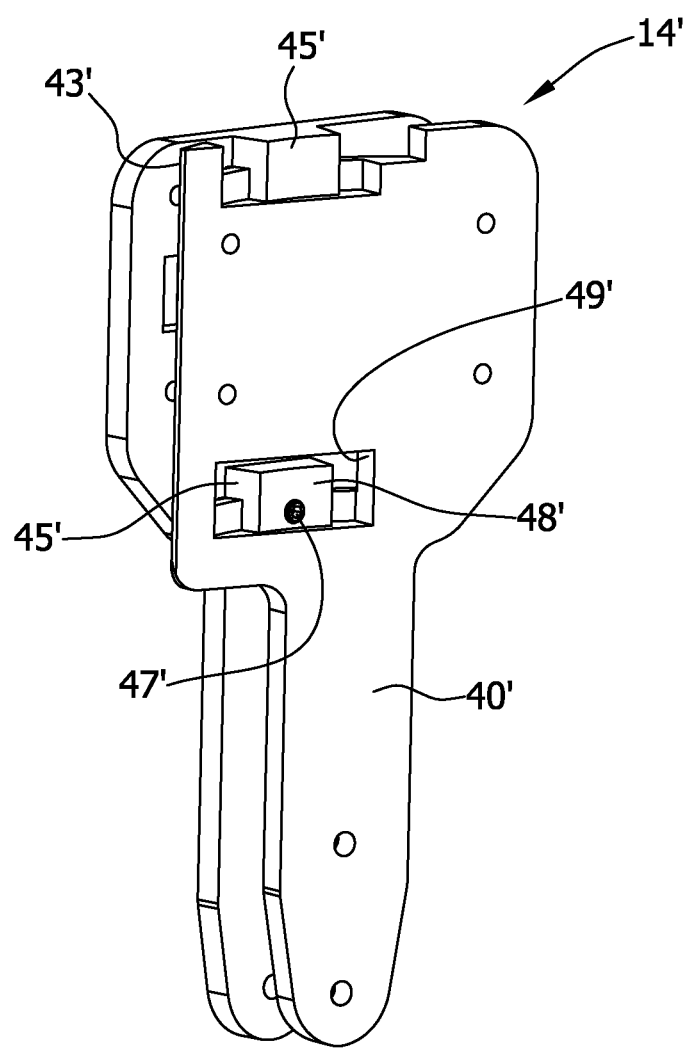
FIG. 7C is an enlarged perspective of the flexion/extension device of FIG. 7B.
Figure 7D:
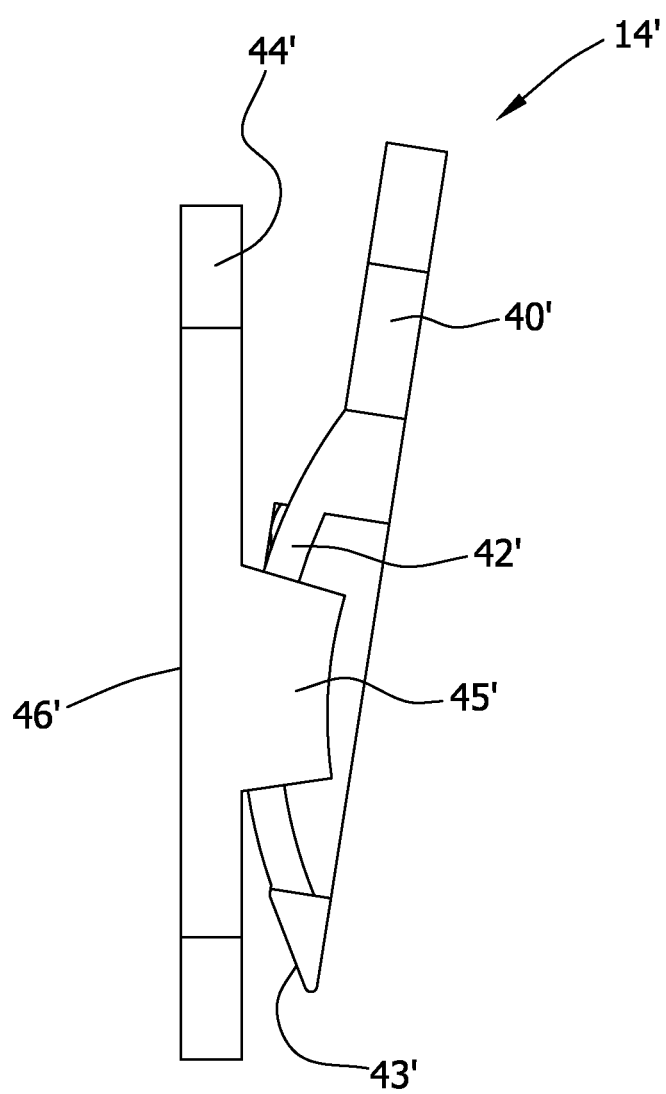
FIG. 7D is a top plan view of the flexion/extension device of FIG. 7C.
Figure 7E:
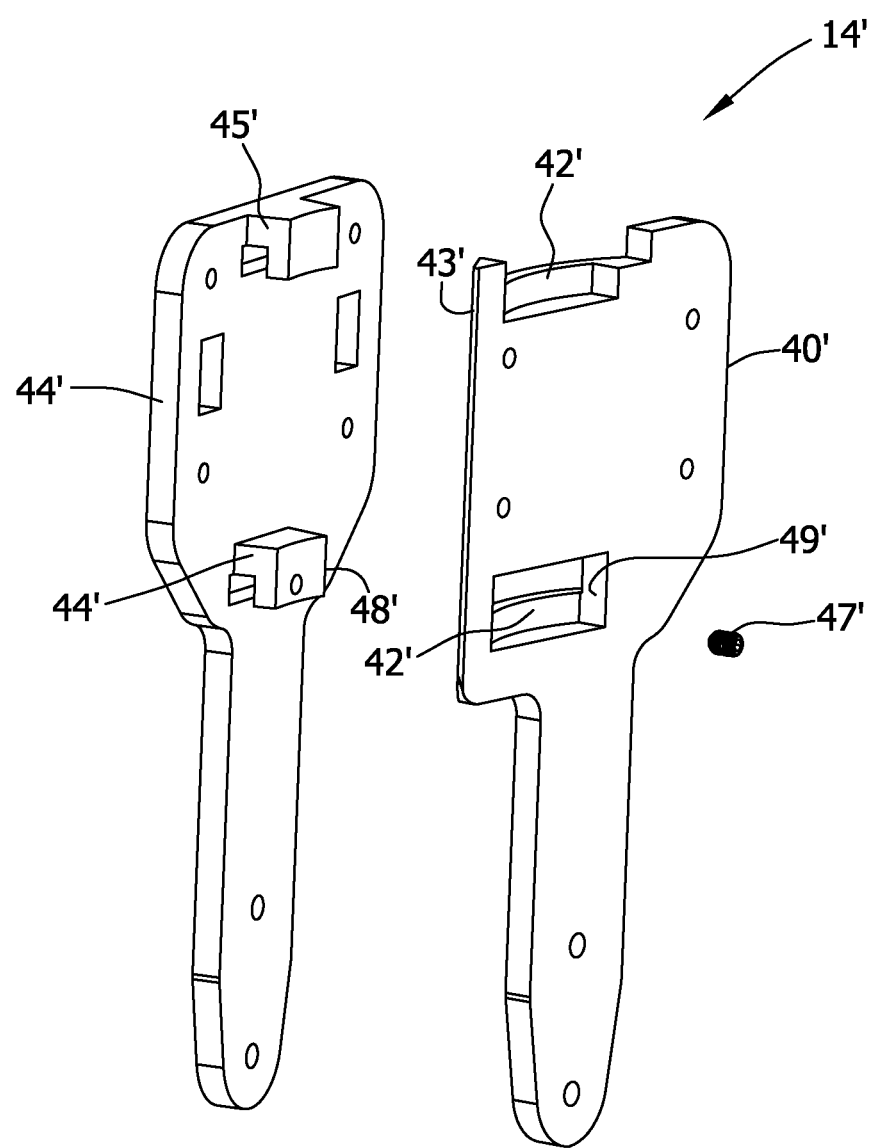
FIG. 7E is an exploded perspective of the flexion/extension device of FIG. 7C.
Figure 7F:
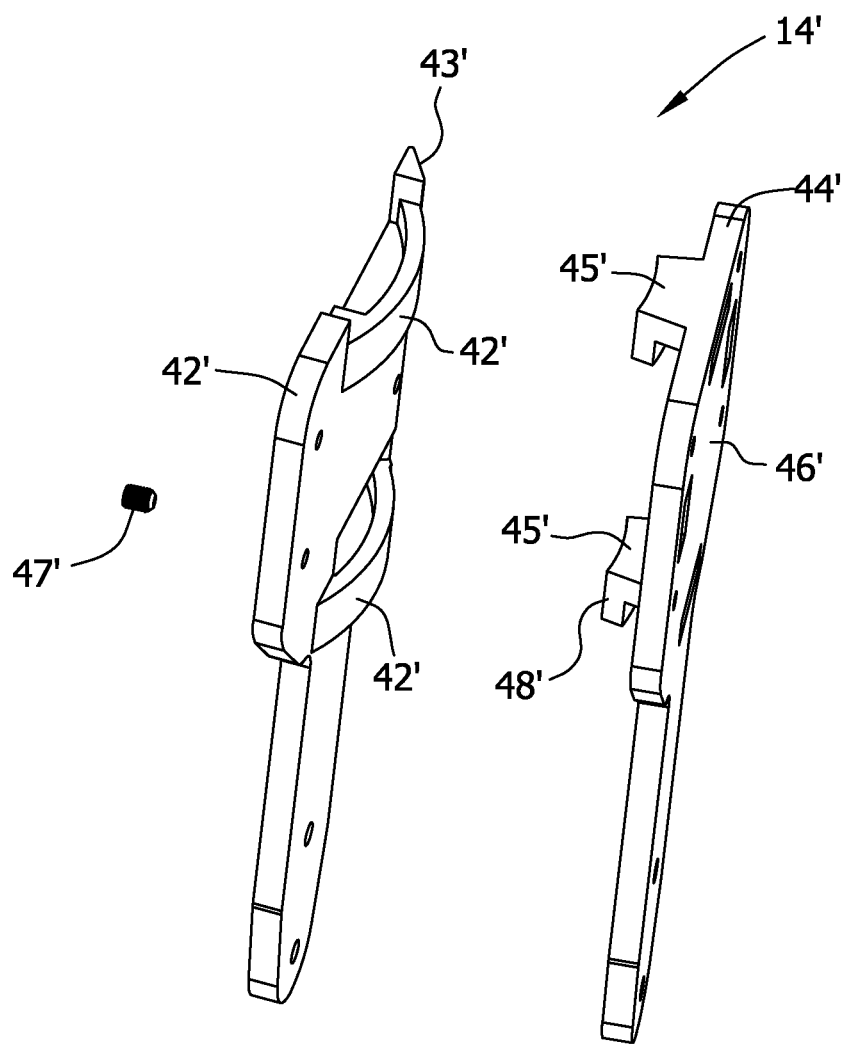
FIG. 7F is an exploded perspective of the flexion/extension device similar to FIG. 7C, except taken from a different viewpoint for illustrative purposes.
Figure 8:
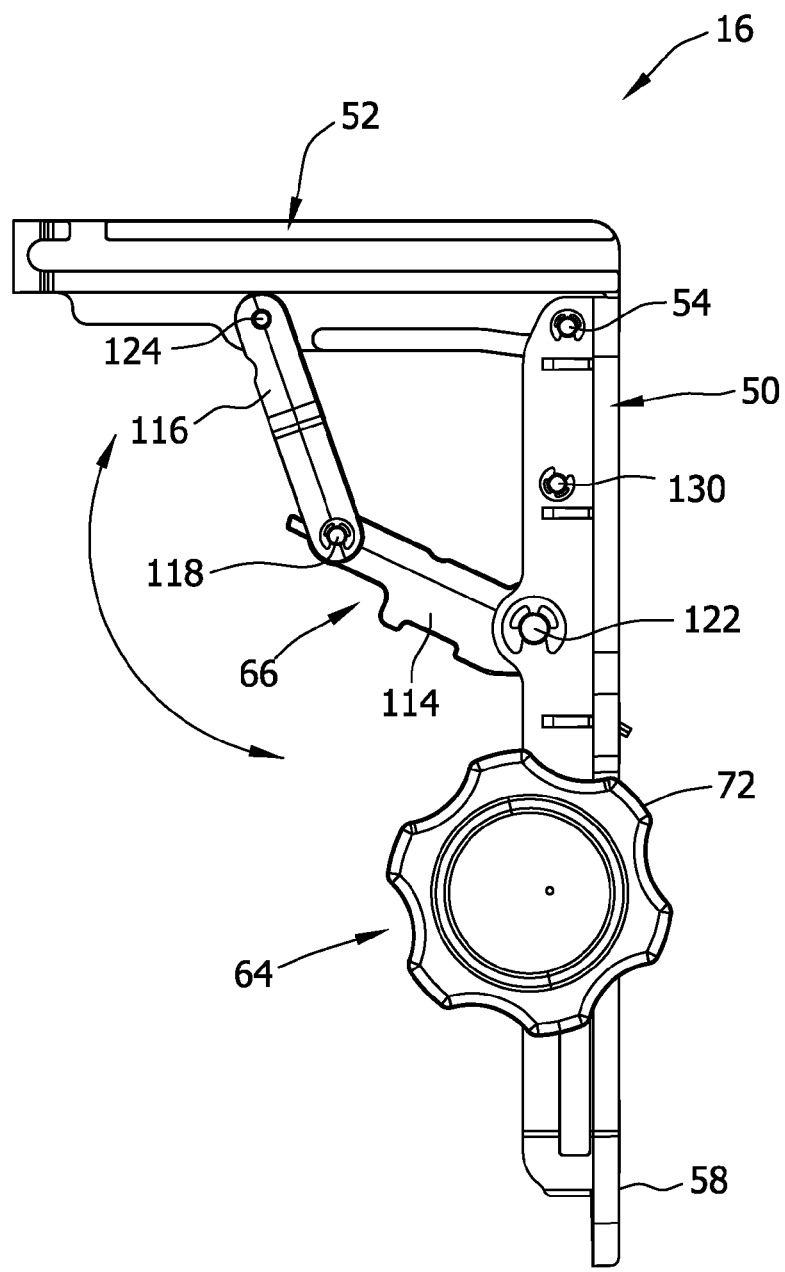
FIG. 8 is an enlarged front elevation of the abduction/adduction device.
Figure 9:
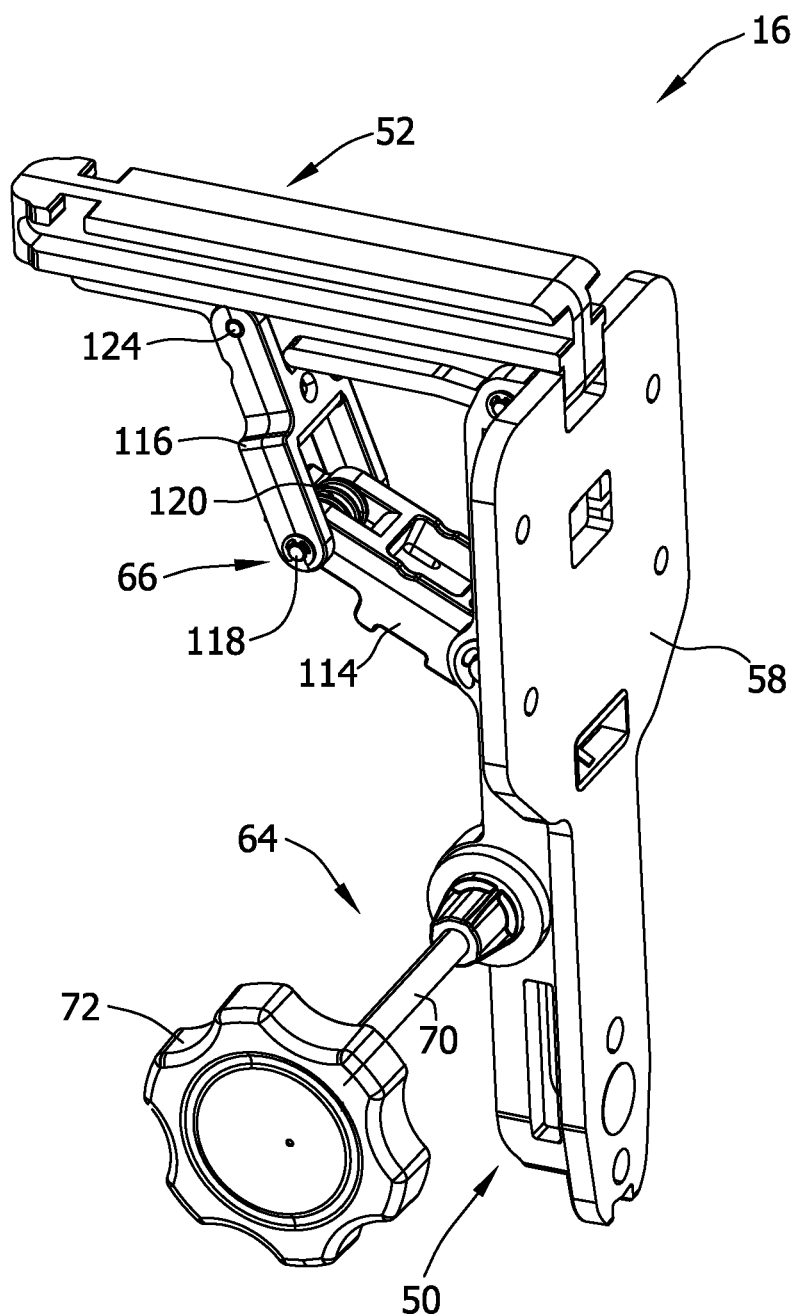
FIG. 9 is a front perspective of the abduction/adduction device of FIG. 8.

A set screw 47' of the flexion-extension device 14' releasably fixes or locks the second load-bearing plate 44' in a selected position on the tracks 42' to facilitate positioning the shoulder joint in a selected degree of flexion and/or extension. The set screw 47' extends through an opening in a free end portion 48' of the lower hook member 48' and engages the lower track 42' to releasable fix the second load-bearing plate 44' on the first load-bearing plate 40'. Loosening of the set screw 47' allows the second load-bearing plate 44' to slide on the tracks 42' for repositioning the second load-bearing plate and adjusting the degree of flexion and/or extension of the shoulder joint. An access opening 49' extending through the first load-bearing plate 40' is substantially aligned with the lower hook member 45' to provide access to the set screw 47' for loosening and tightening the set screw, such as through use of a suitable tool. As seen in FIG. 7B, the access opening 49' is disposed between the thoracic support 20 and the waist support 22 so that it is exposed, at least when the torso-securing device 12 is not secured to the person. Alternatively, an opening can be formed in the torso-securing device. Other ways of releasably locking the position of the second load-bearing plate 44' relative to the first load-bearing plate 40' (more broadly, the position of a shoulder therapy device relative to the torso-securing device 12) do not depart from the scope of the present disclosure.

It is understood that the flexion/extension device 14' may be selectively adjustable in other ways to allow for selective positioning of the shoulder joint in a selected degree of flexion and/or extension, without departing from the scope of the present disclosure. For example, the flexion/extension device 14' may include a simple hinge joint operatively coupling the abduction/adduction device 16 (or other shoulder therapy device) to the torso-securing device 12. In one embodiment, a simple hinge joint may couple the second load-bearing plate 44 to the first load-bearing plate 40. Other configurations do not depart from the scope of the present disclosure.

The adjustable flexion/extension device 14' may be configured to place the shoulder joint in a selected degree of a plurality of degrees ranging from about 5 degrees to about 90 degrees of flexion, more specifically, about 10 degrees to about 60 degrees flexion, or about 15 degrees to about 45 degrees flexion, or about 20 degrees to about 40 degrees, or about 25 degrees to about 35 degrees. In another embodiment, the number of selectable degrees from which the shoulder joint may be discrete and predetermined. For example, the selectable degrees may be 25 degrees, 30 degrees and 35 degrees. In another embodiment, the selectable degrees may be substantially any degree within the range of degrees, and therefore, theoretically the number of degrees is infinite. For example, the selectable degrees may be any degree that within the range (e.g., between 25 degrees and 35 degrees). The illustrated flexion/extension device 14' facilitates placement of the shoulder joint in theoretically any degree of flexion within the range of about 0 degrees to about 30 degrees.

Moreover, the flexion/extension device 14 may be configured to facilitate positioning of the shoulder joint at a selected degree of a plurality of degrees of extension, such as ranging from about 1 degrees of extension to about 10 degrees. The number of selectable degrees of extension may be discrete and predetermined or theoretically infinite, as disclosed above with respect to the degrees of flexion. The flexion/extension device 14 may have other configurations without departing from the scope of the present disclosure.

It is also contemplated that the flexion/extension device 14 may include a drive mechanism to facilitate flexion and/or extension of the shoulder joint to move and position the shoulder joint at a selected degree of flexion or extension. Such drive mechanism may include one of the drive mechanisms employed in the abduction/adduction device 16 and the internal/external rotation device 18. Other suitable drive mechanisms may be used. This particular embodiment allows the flexion/extension device to function as a shoulder therapy device like the illustrated abduction/adduction device 16 and the illustrated internal/external rotation device 18.

It is understood that the flexion/extension device 14 may have other configurations without departing from the scope of the present disclosure. For example, the flexion/extension device may be formed integrally with a portion of a torso securing device, such as being formed integrally with a thoracic support or a waist support. Moreover, the flexion/extension device may be integrally formed with a portion of the abduction/adduction device or another shoulder therapy device.

Abduction/Adduction Device

As used herein, the term "abduction/adduction device" is a device that is configured to position and/or move the shoulder joint in at least one of a selected degree of abduction and a selected degree of adduction or only one of a selected degree of abduction and a selected degree of adduction. The "abduction/adduction device" may be selectively adjustable, to allow for selective adjustment of the degree of abduction/adduction of the shoulder and provide corresponding treatment during abduction and/or adduction, as seen in the embodiments of FIGS. 7-13, or the abduction/adduction device may be non-adjustable, such that the degree of abduction/adduction of the shoulder is substantially fixed at a selected degree (not shown).

Referring now to FIGS. 7-13, the shoulder abduction/adduction device 16 of the illustrated embodiment is generally in the form of an adjustable bracket including a stationary bracket member, generally indicated at 50, which is secured to the flexion/extension device 14 and remains substantially stationary relative to the torso of the person, and a movable bracket member, generally indicated at 52 (broadly, a force-imparting member), which is secured to the internal/external rotation device 18 and moves relative to the torso of the person. The bracket members 50, 52 are hingedly connected to one another by a pivot pin 54 (FIGS. 8, 10 and 13) such that the movable bracket is pivotable toward and away from the fixed bracket member about the pivot pin and within an abduction/adduction plane. In the illustrated embodiment, the stationary bracket member 50 has a securement plate 58 secured to the mounting surface 46 of the second load-bearing plate 44, which is in turn secured to the angular displacement member 42 of the flexion/extension device 14, such that the abduction/adduction plane is offset a non-orthogonal angle (e.g., 30 degrees) relative to a sagittal plane to provide the selected degree of shoulder flexion, as set forth above.

The shoulder abduction/adduction device also includes an abduction/adduction drive assembly, generally indicated at 64, and a force transmitting mechanism, generally indicated at 66, for selectively pivoting the movable bracket member 52 relative to the stationary bracket member 50, to thereby facilitate adduction or abduction of the shoulder joint. In general, the abduction/adduction drive assembly 64 imparts torque to the brackets 50, 52 via the force transmitting mechanism 66.

Figure 10:
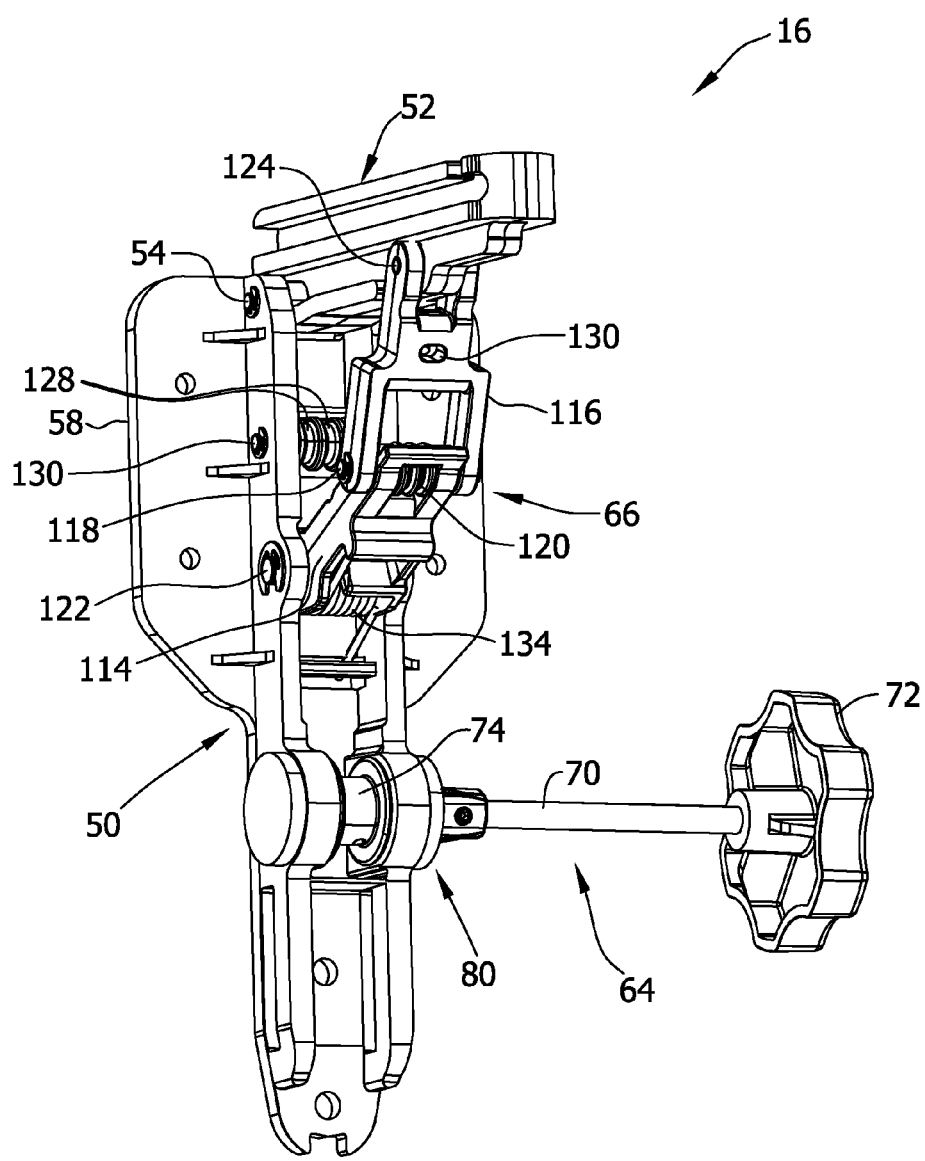
FIG. 10 is a rear perspective of the abduction/adduction device of FIG. 8.
Figure 11:
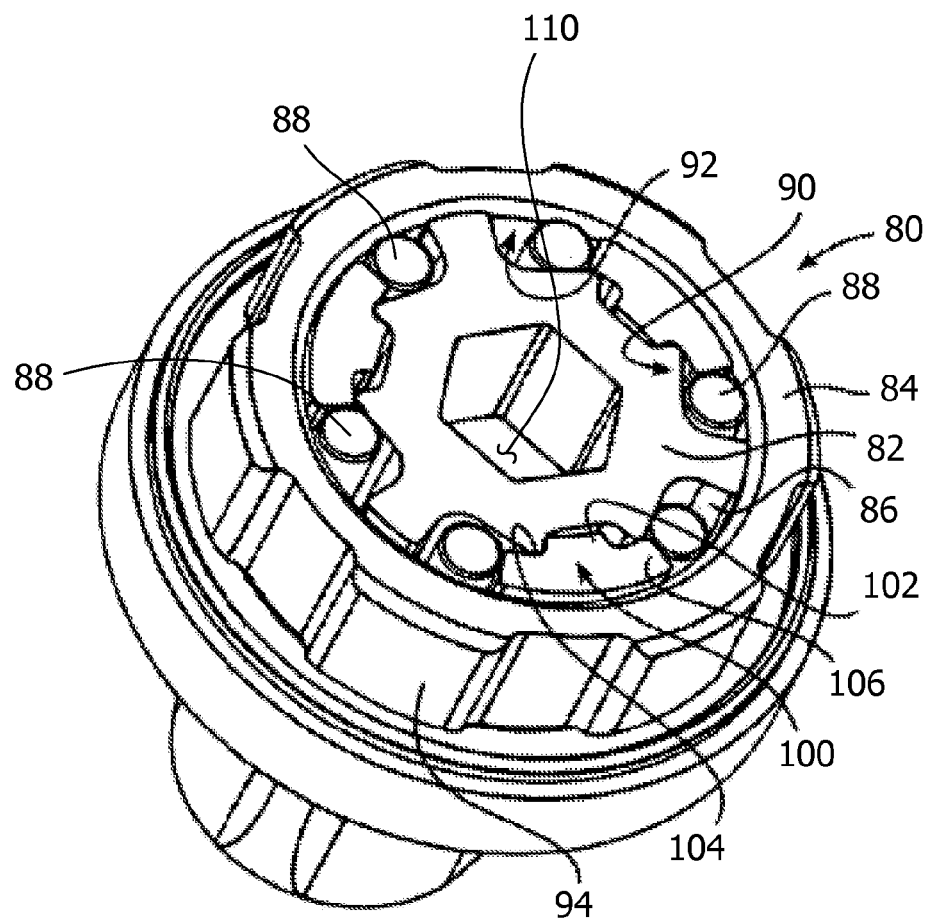
FIG. 11 is an enlarged perspective of a rotation control device of the abduction/adduction device.
Figure 12:
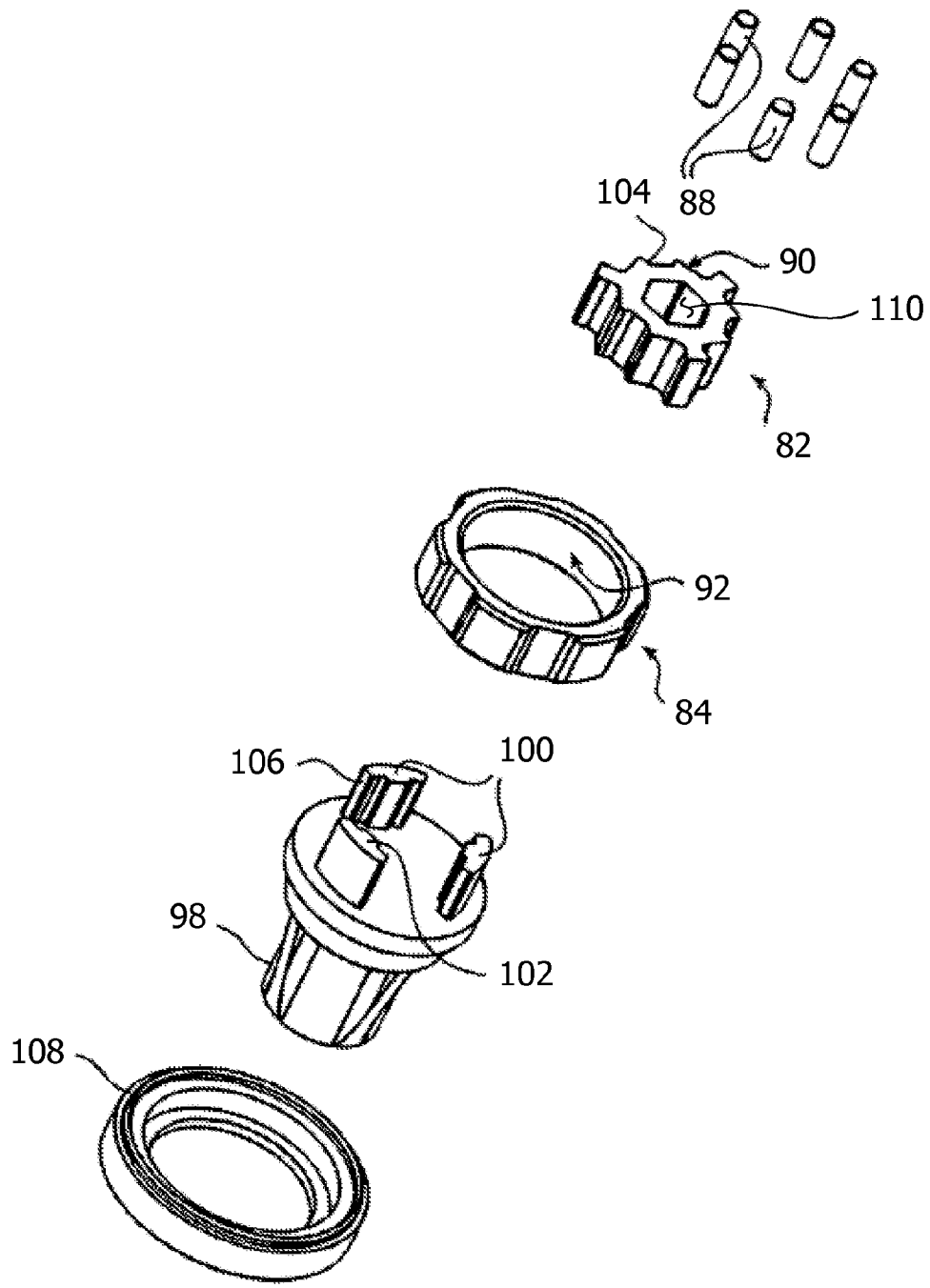
FIG. 12 is an exploded perspective of the rotation control device of FIG. 11.

With particular reference to FIGS. 10-12, the drive assembly 64 includes a drive shaft 70, having a knob or handle 72 that is rotatable by hand. Alternatively, the drive shaft 70 may be driven by a motor (not shown), which may be controlled by servo control circuits, the circuit possibly including a computer with a human interface connected by wires, or a wireless network. The drive shaft 70 is operatively coupled to a spool 74, on which a cable 76 (FIG. 13) of the force transmitting mechanism 66 is wound. As explained in more detail below, the cable 76 is further wound around pulley wheels (identified below) to impart a mechanical advantage to the rotational force applied to the spool 74 by the drive assembly 64.

In one embodiment (see, for example, FIGS. 7-13), a rotational position of drive shaft 70, and thus a selected degree of abduction/adduction of the shoulder joint, is maintained by a rotation control subassembly device, generally indicated at 80, which enables an operator to rotate the drive shaft 70 to adjust a tension of the abduction/adduction device 16, and concomitantly prevents rotation of drive shaft incident to forces imparted by a load. Loading forces include, for example, gravitational forces acting upon the body, or body tissue resisting stretching.

Referring to FIGS. 11 and 12, the rotation control subassembly 80 includes inner and outer raceways, or races 82, 84, respectively, defining peripheral inner spaces 86 therebetween, and rotatable elements, such as pins 88 or spheres, disposed within the spaces 86. When one of races 82, 84 is rotated with respect to the other, the pins 88 are urged along a ramp 90 associated with one of the races, whereby the pins become pinched and bind between the ramp and an inner surface 92 of the outer race 84, thereby preventing further movement, or creating a lock-up condition, of one of the races relative to the other. The ramps 90 are provided for both possible directions of rotation of the inner race 82. The outer race 84 is fixed against rotation, whereby when the races 82, 84 become fixed relative to each other, neither race rotates. Exterior teeth 94 on the outer race 84 are provided to engage a stop (now shown) on the stationary bracket member 50. In this manner, the outer race 84 cannot rotate relative to the abduction/adduction device 16, or the drive assembly 64.

Drive shaft 70 is connected via bushing 98, or other known means, to a series of engagement dogs 100, which are interposed in the spaces 86 between the inner and outer races 82, 83, respectively. When drive shaft 70 is rotated about its axis, bosses 102 associated with the dogs 100 engage cams 104 associated with the inner race 82, whereby drive shaft 70 operates to rotate, or drive, the inner race. The engagement dogs 100 simultaneously impinge at surface 106 upon the pins 88, enabling free rotation of drive shaft 70 by ensuring that the pins 88 do not travel sufficiently far along the ramp 90 to bind between the races 82, 84. In the embodiment illustrated, the inner race 82 bears the ramps 90, however it should be understood that one skilled in the art could switch the roles of the inner and outer ramps, whereby the ramps are disposed upon an inner surface of the outer race 84, and the inner race is fixed. A retainer 108, and other supporting means, may be provided to secure the components of rotation control subassembly 80 together. Additional components may be included, as known by one skilled in the art, to secure subassembly 80 within the drive assembly 64.

A shaft (not shown) is secured within a hex-shaped aperture 110 defined by the inner race 82. The shaft passes axially through the spool 74 to operatively connect the shaft to the spool such that rotation of the shaft imparts rotation of the spool. Broadly, the spool 74 functions as a lever and the cable 76 functions as a tensioning member. It is understood that other devices operative to transmit the rotational force of the drive shaft 70 to the cable 76 may be used, including a bar, eccentric spool or cam, pincher, or grasper. In each case, the rotational force imparted by drive shaft 70 is applied to the other device to cause the device to apply a tensioning force to the cable 76. It is understood that the rotation control subassembly 80 may be of other configurations. Moreover, the shoulder orthosis 10 may not include the rotation control subassembly 80 without departing from the scope of the present disclosure.

In another embodiment (FIG. 13) the drive assembly may include one way clutch comprising fixed, ramped pawl teeth 111, and mating slots 112 within the spool 74, which enable a tensioning rotation in one direction only. A spring 113 urges the spool 74 against the pawl teeth 111. To disengage tension, the spool 74 is pressed, as with fingertips to compress the spring 113 and move the spool away from engagement with the pawl teeth 111, whereupon the spool is substantially free to counter rotate.

As set forth above, the force transmitting mechanism 66 includes the cable 76. Any form of cable or cord, spring, or other force transmitting device as described herein may be used with the force transmitting mechanism 66. Referring to FIGS. 8-10 and 13, in addition to the cable 76, the force transmitting mechanism 66 includes proximal and distal shackles 114, 116, respectively. A clevis pin 118 pivotally couples ends of the proximal and distal shackles 114, 116 to one another at a hinged shackle joint, and further supports at least one pulley wheel 120 at the shackle joint. Respective opposite ends of the proximal and distal shackles 114, 116 are pivotally coupled to the respective stationary and movable bracket members 50, 52, respectively, via respective shackle pins 122, 124. At least two adjacent pulley wheels, each indicated at 128, are secured to the stationary bracket member 50 via a pin 130.

Figure 13:
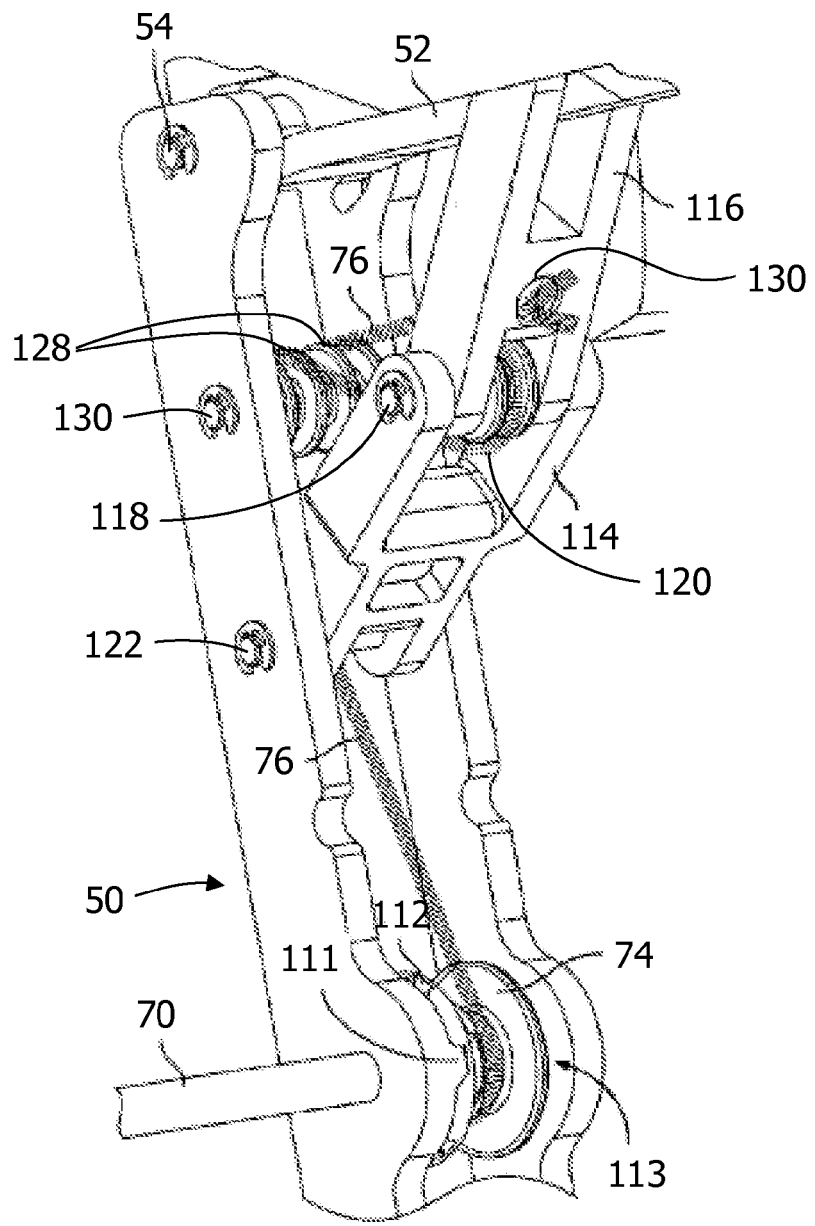
FIG. 13 is an enlarged fragmentary perspective of another embodiment of the abduction/adduction device.
Figure 14:
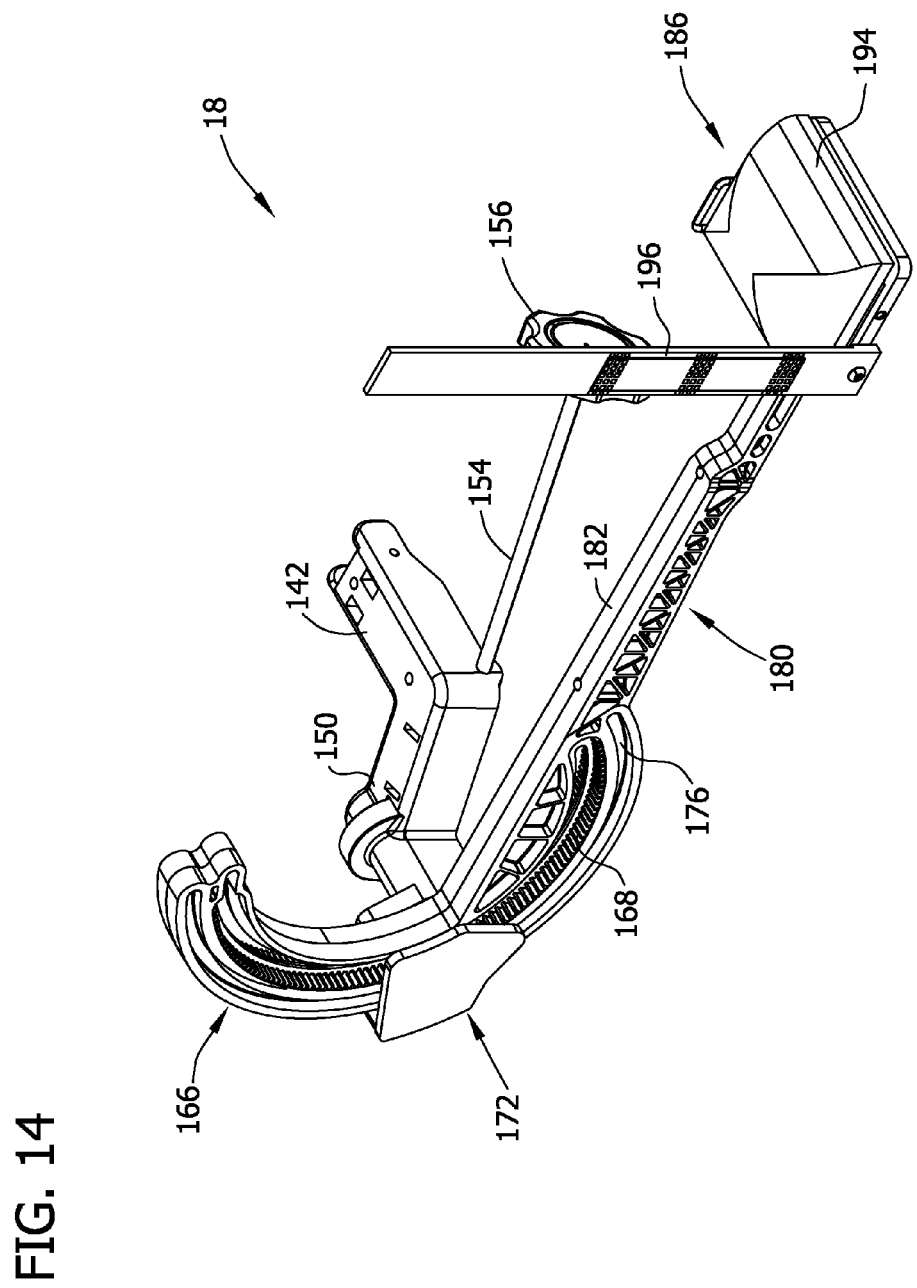
FIG. 14 is an enlarged perspective of the internal/external rotation device.

As seen in FIG. 13, the cable 76, which is affixed to and at least partially wound around the spool 74, as set forth above herein, is partially wound around each of the pulley wheels 120, 128 and is tethered to the distal shackle 114, such as by a tying a knot at the free end of the cable, after inserting the free end through an aperture 130 in the distal shackle. The manner of affixing the cable 76 may be varied. The pulley configuration described operates to pull the clevis pin 118 towards the hinged connection of the bracket members 50, 52 as the spool 74 is wound in a tightening direction. The pulley wheels 120, 128 operate together to increase the mechanical advantage of the force applied to spool 74, facilitating operation by a user. For example, in the embodiment shown, a mechanical advantage is obtained resulting in one third less force required to rotate the knob 72. Other pulley configurations may be employed within the scope of the disclosure, as would be understood by one skilled in the art.

With reference to FIG. 10, a torsional spring 134, received on the shackle pin 122, is operative to maintain a minimum tension on the cable 76, to reduce entanglement, and to maintain the cable in proper engagement with the pulley wheels 120, 128 when the cable is not in tension. The spring 134 urges the proximal shackle 114 away from the hinged connection between the bracket members 50, 52. The spring 134 may further be selected to apply a therapeutic force, in addition to a resilient force of the cable 76.

While the hinged shackles 114, 116 are described in connection with changing an angle of bracket members 50, 52, it should be understood that other methods may be employed, as are known in the art or which may be discovered. For example, a cantilever (not shown) may extend from a bracket member, acted upon by cable connected at a cantilever extremity.

The cable 76 may be composed of any of a variety of materials, including natural or synthetic fibers, solid, wound or braided materials, or other durable and flexible material selected for a desired resiliency based upon an intended therapeutic application. Examples include cotton or polypropylene cord, plastic tape or strands, wire wound spring or woven wire fabricated from stainless steel or shape metal alloy material, and rubber or latex containing material. Accordingly, the resiliency of the cable may be selected by the type of material, as well as how it is prepared. In accordance with the disclosure, a cable may be selected to exhibit a significant resistance to stretching, such as a steel cable, or the ability to stretch considerably, such as a rubber or latex cable. The practitioner may thus select a cable resilience to correspond to the therapeutic objective. Additionally, depending on the materials and configuration of the orthosis 10, resiliency may be contributed by the device itself, wherein a cable is selected in consideration of the observed resiliency of the device as configured.

Referring to FIG. 1A through FIG. 5, an upper arm securing device, generally indicated at 140, is operatively connected to the movable bracket member 52. The upper arm securing device 140 includes a support 140a and a releasable strap 140b that positions the longitudinal axis of the upper arm within a plane that is generally coplanar with the abduction/adduction plane. The upper arm securing device 140 is configured to inhibit anterior and posterior movement of the upper arm, while allowing the upper arm to rotate about its axis when the upper arm is secured thereto. In the illustrated embodiment (seen in FIGS. 4 and 5), the upper arm securing device 140 is secured to a telescoping extension member 142 of the internal/external rotation device 18. The extension member 142 is telescopingly connected to the movable bracket member 52, and in turn, to the abduction/adduction device 16. More specifically, the telescoping extension member 142 is slidably coupled to the movable bracket member 52 by a tongue and groove connection to allow for adjustment of the distance between the internal/external rotation device 18, and in turn the upper arm securing device 140, and the torso securing device 12 to accommodate various arm lengths. A set screw 144 is used to fix the selective position of the telescoping extension member 142 on the movable bracket member 52.

During use of the abduction/adduction device 16, the drive shaft 70 is rotated, such as by using the knob 72, to increase the angle between the proximal and distal shackles 114, 116, and in turn, move the movable bracket member 52 away from the stationary bracket member 50. Movement of the movable bracket member 52 away from the stationary bracket member 50 imparts abduction of the shoulder joint, which stretches tissue associated with the shoulder joint. Movement of the movable bracket member 52 toward the stationary bracket member 50 imparts adduction of the shoulder joint, which may also stretch tissue associated with the shoulder joint. During static stretching, as tissue stretches, the force required to maintain a stretched position decreases, and may ultimately fall to zero. If the cable 76 is resilient, however, a minimum amount of dynamic stretching force is maintained throughout the stretching period. The amount of dynamic stretching force is a function of the resiliency of cable 76.

In one example, the abduction/adduction device may be configured to facilitate selective abduction and adduction and positioning of the shoulder joint from about 0 degrees of abduction to about 90 degrees of abduction. The abduction/adduction device may facilitate a different range-of-motion of the shoulder without departing from the scope of the present disclosure.

Internal/External Rotation Device

Figure 15:
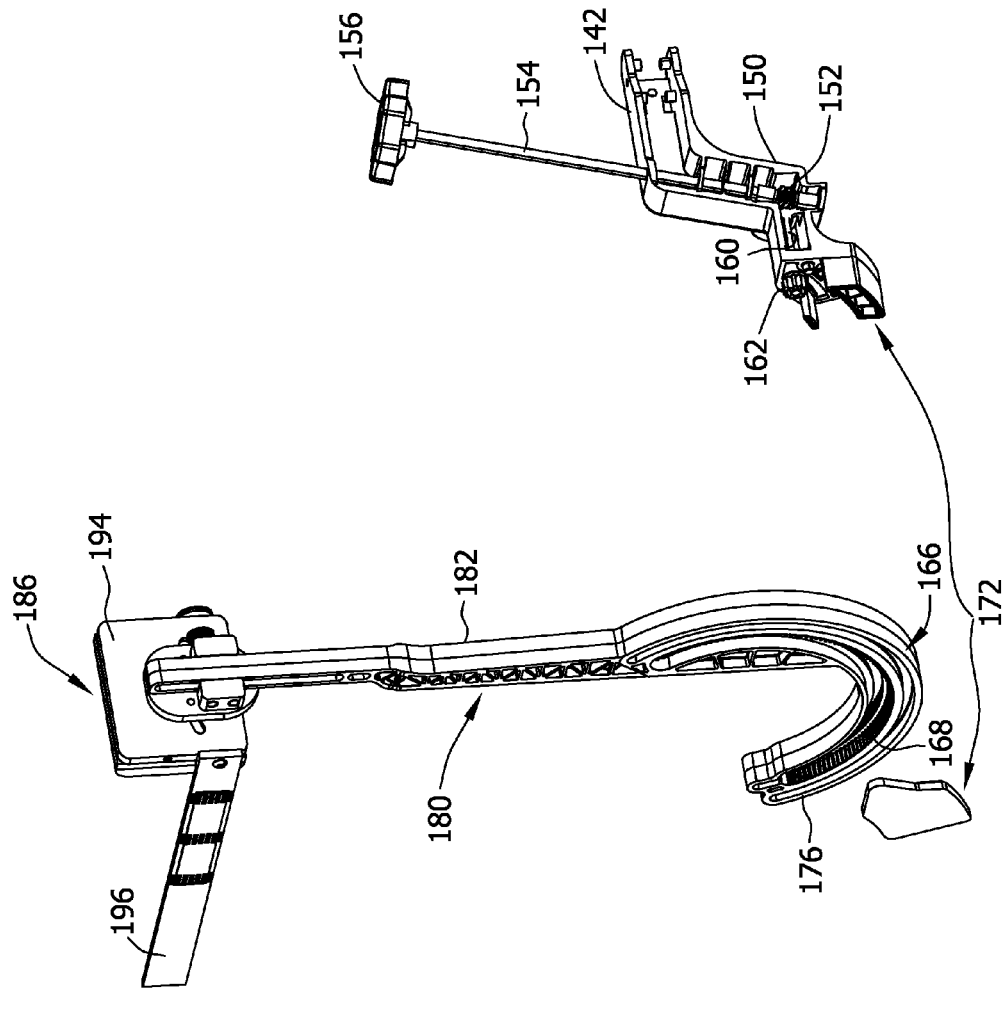
FIG. 15 is an exploded, bottom plan view of the internal/external rotation device of FIG. 14.
Figure 16:
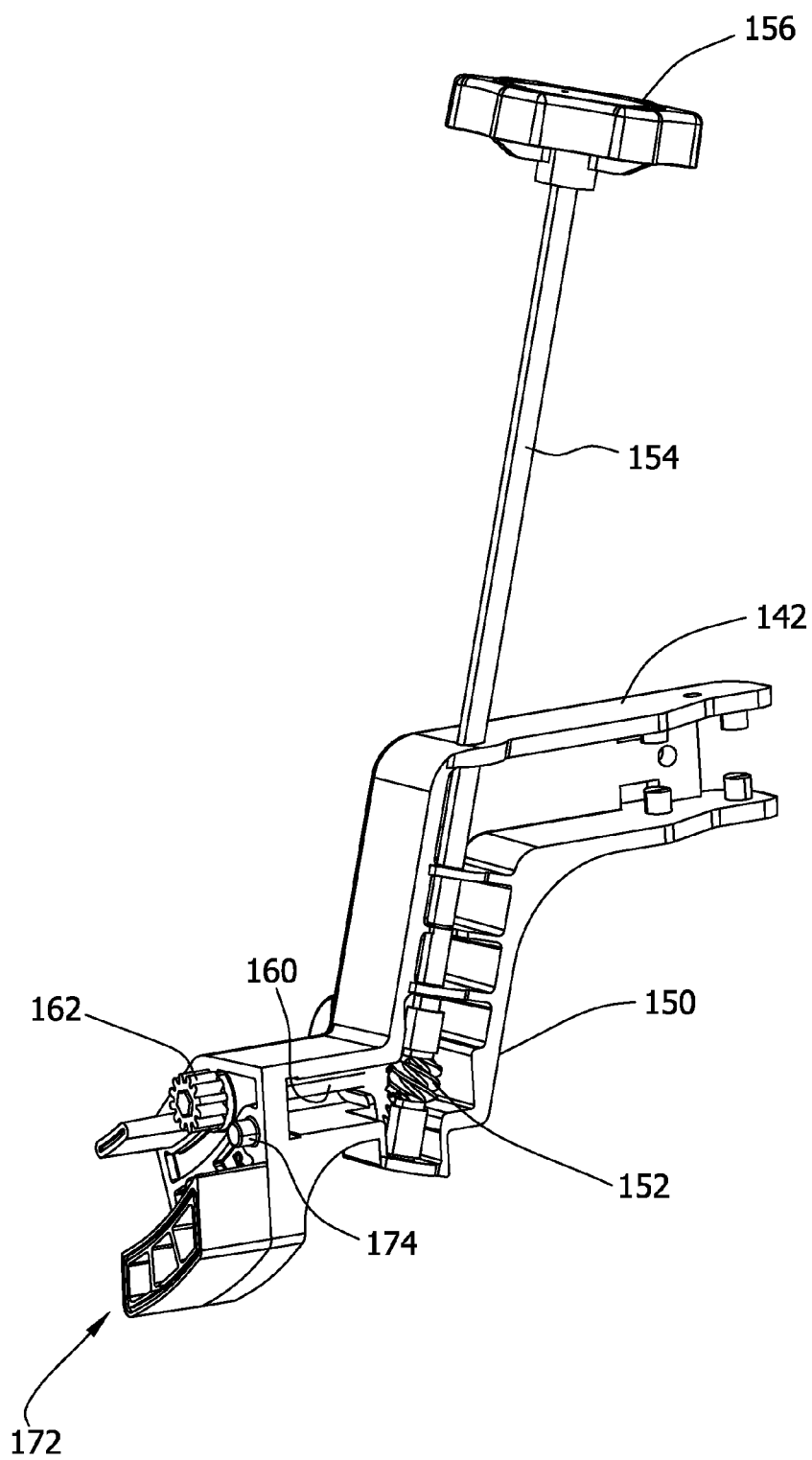
FIG. 16 is a bottom perspective of a gearbox of the internal/external rotation device of FIG. 14 including a drive mechanism.
Figure 17:
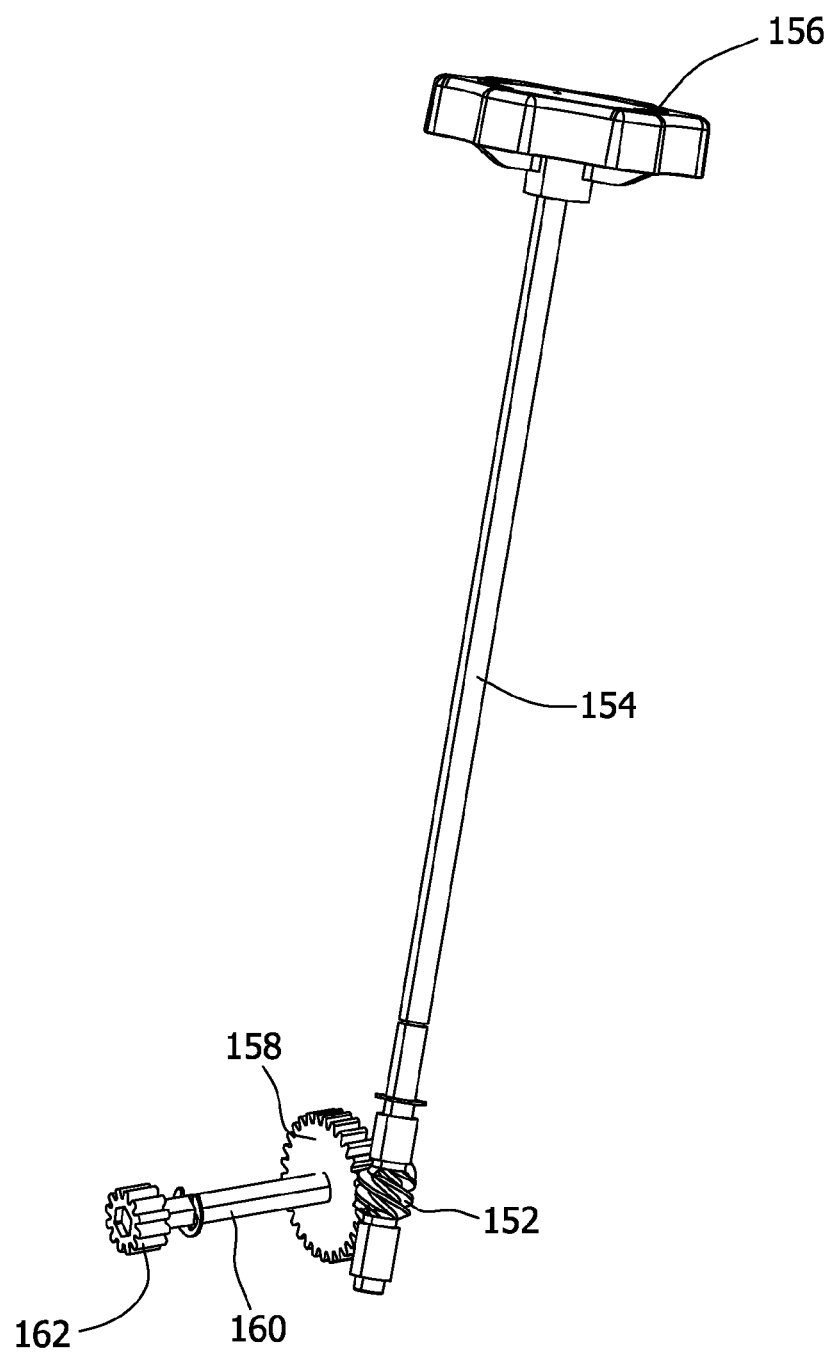
FIG. 17 is similar to FIG. 16, except that the gearbox is removed.

With particular reference to FIGS. 14-17, the internal/external rotation device 18 includes an L-shaped gearbox, generally indicated at 150, connected to, e.g., integrally formed with, the telescoping extension member 142. As seen in FIGS. 16 and 17, the gearbox 150 houses an input gear 152 operatively connected to an end margin of an input shaft 154 having a knob or handle 156 at an opposite end. A transmission gear 158 (FIG. 17) engages the input gear 152. In the illustrated embodiment, the input gear 152 is a worm, and the transmission gear 158 is a worm gear, although the transmission gear may be a worm, and the input gear may be worm gear. Other configurations do not depart from the scope of the present disclosure.

Referring to FIGS. 15-17, the transmission gear 158 is operatively connected to a drive shaft 160, which drives an output pinion gear 162. The pinion gear 162 engages an arcuate rack gear, generally indicated at 166, which includes teeth 168 that are arranged along an arcuate path, which may or may not generally follow the overall shape of the rack gear. As the knob 156 of the input shaft 154 is rotated, the rotational movement is translated through the input gear 152 and the transmission gear 158 to turn the drive shaft 160, thereby turning the pinion gear 162 and driving the rack gear 166 along an arcuate path. A rack support member, generally indicated at 172, supports the rack gear and operatively connects the rack gear to the gearbox 150. The support member 172 includes at least one projection or tongue 174 inserted into smooth, arcuate shaped grooves or tracks 176 in the rack gear 166. The tracks 176 generally follow the arcuate path of the teeth 168 and provide support and guidance for the rack gear as it is driven by the pinion gear 162.

A force-imparting member, generally indicated at 180, of the internal/external rotation device extends outward from the rack gear 166. The force-imparting member 180 moves with the rack gear 166, along the arcuate path of the rack gear, and is configured to impart or transmit force from the rack gear to a forearm and a hand of the person that is secured to the force-imparting member. The force-imparting member 180 includes a substantially rigid, cantilever arm 182 and forearm and hand securing devices 184, 186, respectively, secured to the arm. The arm 182 has a longitudinal axis lying substantially coplanar with the teeth 168 of the rack gear 166. The forearm securing device 184 removably secures the forearm of the person to the internal/external rotation device and imparts the force of the cantilever arm 182 to the forearm. In the illustrated embodiment, the forearm securing device 184 comprises a support 190 and an adjustable strap 192 (together referred to as a cuff), which restricts the forearm and the elbow from lifting out of position relative to the internal/external rotation device 18 as a therapeutic force is applied. The hand securing device 186 is telescopingly connected to the distal end of the cantilever arm 182. The hand securing device 186 comprises a support 194 (e.g., a pad) and an adjustable strap 196, which restricts the hand, and further restricts the forearm and elbow, from lifting out of position as a therapeutic force is applied. The support 194 is selectively slidable along the axis of the cantilever arm 182, such as by a tongue and groove configuration and a set screw, allowing for various forearm lengths. The force-imparting member 180 may also include an elbow support for supporting the elbow.

Referring to the internal/external rotation device, as knob 156 is rotated, internal or external (medial or lateral) rotation of the shoulder joint is effectuated. The cantilever arm 182 rotates within an internal/external rotation plane. In the illustrated embodiment, the orthosis 10 is configured such that the elbow is maintained at 90 degrees of flexion when the person's arm is properly secured to the orthosis. The elbow may be flexed at another angle, other than 90 degrees, without departing from the scope of the present disclosure. It is also understood that the degree of elbow flexion may be adjustable. Moreover, when the person's arm is properly positioned, the pivot point of internal/external rotational device 18 is along the axis of the upper arm.

In one example, the internal/external rotation device may be configured to facilitate selective internal rotation and positioning of the shoulder from about 0 degrees to about 90 degrees of internal rotation. Moreover, the internal/external rotation device may be configured to facilitate selective external rotation and positioning of the shoulder from about 0 degrees to about 90 degrees of external rotation. The internal/external rotation device may facilitate a different range-of-motion of the shoulder without departing from the scope of the present disclosure.

When stretching tissue of the shoulder, internal/external rotation angle is set for optimized beneficial effect with respect to the glenohumeral joint. The internal/external rotation angle may be changed to alter to application of force at the glenohumeral joint. Moreover, the internal/external rotation angle may be changed to effectuate a therapeutic benefit upon the elbow. It should further be understood that effectuators as are known and described in the art may be fitted to the wrist portion of device 10 in order to carry out stretching therapy upon the wrist.

Exemplary Materials for Fabrication

Devices may be made using flexible or rigid polymeric material, metal, or other biocompatible materials capable of exerting loading when flexed, stretched or compressed. An exemplary orthosis, including a flexible section is disclosed in U.S. Pat. No. 5,685,830 entitled "Adjustable Orthosis having one-piece connector section for flexing" to Bonutti, the contents of which are herein expressly incorporated by reference in their entirety.

The components of the disclosure that are rigid members made of, for example, aluminum, stainless steel, polymeric, or composite materials. The member and extensions are sufficiently rigid so as to be able to transmit the necessary forces, and cooperate to provide a resilient force, where dynamic tension is desired. It should be understood that any material of optimal rigidity can be used. More particularly, a resilient frame may advantageously be employed to contribute a continuous force to the joint, cooperating with a resilient cable, or providing the sole resilient force for stretching tissue associated with a joint.

Flexible sections can be made of a shape memory or reactive material, where a change in temperature, or application of an electrical current, results in a shape or position change of the flexible section. The change in shape of a flexible section can be used to change the position of adjacent frame brackets. Alternatively, the change in shape of a flexible section can be used to provide a force to adjacent frame brackets.

For example, the components can be made by injection molding. Generally for injection molding, tool and die metal molds of the components are prepared. Hot, melted plastic material is injected into the molds. The plastic is allowed to cool, forming components. The components are removed from the molds and assembled. In addition to being bolted together, portions of the device in accordance with the invention may be assembled by welding, adhesives, or other means. In addition, adjustable connections may be achieved by clamps, springs, hook and loop fasteners, and other removable means.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such an instance, the device can be used as a positioning device for use in imaging devices, such as a MRI device. It is also contemplated that the device can be used as a positioning device for use during surgical procedures, where it may be necessary to adjust and hold the position of the joint.

Exemplary Methods of Using Embodiment(s) of the Orthosis

In an exemplary use, the shoulder orthosis 10 is operated to extend the shoulder joint in the following manner. The torso securing device 12 is secured to the person, such as in the manner set forth above. The person's upper arm, forearm, and hand are then attached to the orthosis 10, such as in the manner set forth above. In an illustrated embodiment, seen in FIGS. 1A and 1B, the person's shoulder joint is in a selected flexion (e.g., 30 degrees of flexion) upon securing the person's arm to the orthosis 10. Adduction and or abduction of the shoulder joint can then be actuated (or selected before securing the arm to the orthosis) by rotating the knob 72. Either the person himself/herself or an assistant can rotate the knob 72. Rotating the knob 72 causes connective tissue of the joint to be stretched. The orthosis 10 may be maintained in a position for a predetermined treatment time, utilizing the principles of stress relaxation to stretch the connective tissue of the joint. Where the cable 76 is resilient, an application of force restricts a relaxation of the connective tissue of the joint, utilizing the principles of creep to further stretch the connective tissue of the joint. After the expiration of the treatment time, the orthosis 10 may be returned to an initial position, relieving the joint. While in one embodiment, the loading or forces applied are substantially constant, they also may gradually increase, decrease, pulse between a first and second amount of force, or be varied in other ways such as described in the cited references.

Optionally, knob 72 can be rotated to a third or additional positions, further increasing the stretch of the connective tissue of the joint, for example at discrete time intervals to incrementally increase the stretch of the joint through the treatment cycle. In each of the movements, the cable 76 provides a substantially constant force to the joint, preventing a relaxation of the connective tissue of the joint. After completion of the treatment cycle, the knob may be counter rotated, and the spool 74 may be moved away from engaging pawls, as described above, to relieving tension on the joint.

Internal and/or external rotation of the shoulder joint can be actuated by rotating the knob 156 of the internal/external rotation device 18. Either the person himself/herself or an assistant can rotate the knob 156. Internal or external rotation of the shoulder can be actuated when the shoulder is in a selected degree of adduction. Rotating the knob 156 causes connective tissue of the joint to be stretched. The orthosis 10 may be maintained in a position for a predetermined treatment time, utilizing the principles of stress relaxation to stretch the connective tissue of the joint. A resilient type of an application of force may be used to prevent a relaxation of the connective tissue of the joint, utilizing the principles of creep to further stretch the connective tissue of the joint. After the expiration of the treatment time, the orthosis 10 may be returned to an initial position, relieving the joint. While in one embodiment, the loading or forces applied are substantially constant, they also may gradually increase, decrease, pulse between a first and second amount of force, or be varied in other ways such as described in the cited references. The shoulder joint can be moved to a third or additional positions.

The force applied in one treatment interval may differ in degree, profile, or duration of force applied in another treatment interval, although in some cases the applied force may be substantially the same for two or more, or even for all treatment intervals.

The degree of force applied, for example, may be varied from one treatment interval to another, and likewise the degree of force applied may be adjusted depending upon different factors or patient needs.

Additionally, adjustments also may be made during a treatment interval. For example, adjustments may be made during a treatment interval in order to increase or decrease the forces imparted, even though the geometric angle or position of the device remains unchanged. In one example, the initial force imparted at the beginning of a treatment interval may be low, but then increased over time according to a patient's progress or according to a predetermined time schedule. In another example, it may be desirable to initially apply a greater force in order to help accelerate a patient's progress, but then later relieve or reduce the forces applied after achieving a satisfactory degree of stretching or after a predetermined time.

In addition, the flexion/extension device 14, and/or the abduction/adduction device 16 and/or the internal/external rotation device 18 can include a force control system for control of the force applied, as in an automated control for the respective drive assemblies. A pneumatic or hydraulic system, for example, may have controls for the amount of force imparted by any or all of the force elements as well as the force profile and direction of applied forces. Likewise, a servo-mechanical force control system may be used to vary the amount of deflection or preload of spring-like force elements. These auxiliary systems could be under control of a computer. The computer could control joint stretching based upon sensors, including sensing of physiological indicators.

In an embodiment, an electric motor (not shown) may be operatively connected to one or more of the flexion/extension device 14, the abduction/adduction device 16, and the internal/external rotation device 18. A battery (not shown) may provide electric power to the motor, or it may be powered from another source. A microprocessor (not shown) can be used to operate the motor to more accurately control positioning of the device, or to allow for automation of some steps of treatment such as moving from one position to another. The motor may also operate within a control system that allows for remote operation of the device by a healthcare professional or technician. The microprocessor and motor together can be used to cycle the devices to move the shoulder joint within a range-of-motion, hold a position while tissue stretches, then move further in that direction; or in any other manner. In another manner of use, the orthosis can be set to cycle to one end of the joint's range-of-motion and hold there for a predetermined period of time, then cycle to the other end of the joint's range-of-motion and hold there. Given the benefit of this disclosure, one may program and control the microprocessor so that desired motion is attained. This embodiment is ideally suited for continuous passive motion exercise, because it can be programmed with the desired sequence of movements. Preferably, at least this embodiment also would be a portable device so that it may be provided to a patient to use in the home, at work, or wherever they may desire.

It should be understood that the particular physical arrangement of the motor, the battery, and the microprocessor may be varied, as known in the relevant art. Additionally, another type of actuation, other than an electric motor, can also be used. For example, the use of a hydraulic or pneumatic motor as the drive mechanism is contemplated.

Another embodiment can include a monitor for use with device 10, which provides assurances the person is properly using device 10 during his/her exercise period. For instance, the monitor can have a position sensor, a temperature sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly. This analysis may be conducted remotely, thereby saving the time and expense of a home visit by a healthcare professional or technician. An exemplary monitoring system is provided in U.S. Publication No. 2004/0215111 entitled "Patient Monitoring Apparatus and Method for Orthosis and Other Devices," to Bonutti et al., the content of which is herein expressly incorporated by reference in its entirety One or more embodiments of the orthosis 10 can be custom made to fit a particular individual, or can be an off the shelf item. One or more embodiments of the orthosis 10 can also be used, for example, to eliminate contractures or stress soft tissue. It can be used for patients with cerebral palsy, stroke, spastic paralysis, burns, as well as in post-traumatic or post-surgical cases. As previously discussed, the orthosis 10 also may be used to extend the rotational capability of a joint. Additionally, the device can be used for tissue transport, bone lengthening, stretching skin or tissue fascia, etc. For example, device of the invention can be incorporated in an external bone fixation device, such as an Ilizarov device, where the device is affixed to the bones on the body portions using pins.

Furthermore, one or more embodiments of the orthosis 10 is disclosed as utilizing the principle of stress relaxation, and in some instances, creep. However, it is contemplated that one or more embodiments of the orthosis 10 can include additional treatment protocols. For example, in continuous passive motion ("CPM"), the device continually moves the joint through a range-of-motion. The motion may be provided by an electric or hydraulic motor or a pneumatic system attached to the device. As the CPM moves the joint through its range-of-motion, however, it may be less effective in increasing the range of motion.

One or more embodiments of the orthosis 10 can be incorporated into a CPM device, where the CPM device would stop at an end range position. As previously discussed, a drive assembly may be provided to move the joint from its normal position at the end range position of the CPM to a second position, thereby stretching the tissue using the principles of stress relaxation. As the tissue relaxes, a force application assembly may be utilized to provide an additional force, utilizing the principles of creep to stretch the tissue. After a set time period, the drive assembly may be moved to a third position to further stretch the tissue or the CPM device may resume movement of the joint through the range-of-motion. Before CPM movement resumes, the drive assembly may be returned to an original position so that the range-of-motion of the CPM is returned to its original state, or the drive assembly may be used to alter the range-of-motion that the CPM follows. In this manner CPM device can be utilized to increase the range-of-motion of the joint.

It should be understood that the static and dynamic portions of one or more embodiments of the orthosis 10 as shown and described herein may both be statically adjustable, or both be dynamically adjustable, as defined herein.

When introducing elements of the present invention or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A shoulder orthosis comprising:
a shoulder therapy device adapted to provide treatment to a shoulder joint of a person; and
a flexion/extension device configured to position the shoulder joint in at least one of greater than 0 degrees of flexion and greater than 0 degrees of extension concurrently with the shoulder therapy device providing the treatment to the shoulder joint, wherein the flexion/extension device includes a load bearing member and an angular positioning member having a mounting surface, wherein the load bearing member lies substantially within a sagittal plane of the person and the mounting surface is angularly offset from the sagittal plane of the person when the shoulder therapy device is secured to the person.

2. The shoulder orthosis set forth in claim 1, wherein the flexion/extension device is configured to position the shoulder joint in greater than about 5 degrees of flexion.

3. The shoulder orthosis set forth in claim 2, wherein the flexion/extension device is configured to position the shoulder joint in greater than about 15 degrees of flexion.

4. The shoulder orthosis set forth in claim 1, wherein the flexion/extension device is configured to position the shoulder joint in about 30 degrees of flexion.

5. The shoulder orthosis set forth in claim 1, wherein the shoulder therapy device comprises an internal/external rotation device configured to selectively facilitate at least one of internal rotation of the shoulder joint and external rotation of the shoulder joint.

6. The shoulder orthosis set forth in claim 1, wherein the shoulder therapy device includes an abduction/adduction device configured to selectively facilitate at least one of abduction of the shoulder joint and adduction of the shoulder joint.

7. The shoulder orthosis set forth in claim 1 further comprising a torso securing device configured for removable securement to a torso of the person, the torso securing device operatively connected to the shoulder therapy device and the flexion/extension device.

8. The shoulder orthosis set forth in claim 7, wherein the flexion/extension device operatively connects the shoulder therapy device to the torso securing device.

9. The shoulder orthosis set forth in claim 8, wherein the torso securing device includes a thoracic support that is configured to engage the lateral thorax of the person, and wherein the load bearing plate is arranged to lie substantially within a sagittal plane of the person when the torso securing device is secured to the torso of the person, and the angular positioning member having a mounting surface that is configured to angularly offset from the sagittal plane of the person when the torso securing device is secured to the torso of the person.

10. The shoulder orthosis set forth in claim 1, further comprising an abduction/adduction device configured to selectively position the shoulder joint in a selected degree of abduction greater than about 5 degrees of abduction, wherein the shoulder therapy device comprises an internal/external rotation device configured to selectively facilitate at least one of internal rotation of the shoulder joint and external rotation of the shoulder joint, wherein the flexion/extension device is configured to position the shoulder joint in about 30 degrees of flexion.

11. The method set forth in claim 1, wherein said operating the shoulder therapy device comprises operating the shoulder therapy device to facilitate at least one of abduction, adduction, internal rotation, and external rotation of the shoulder joint.

12. The shoulder orthosis set forth in claim 1, wherein the flexion/extension device is selectively adjustable to facilitate selective positioning of the shoulder joint in one of a plurality of different degrees of flexion.

13. The shoulder orthosis set forth in claim 12, wherein the plurality of different degrees of flexion is within a range of about 0 degrees of flexion and about 60 degrees of flexion.

14. The shoulder orthosis set forth in claim 13, further comprising an abduction/adduction device configured to selectively facilitate at least one of abduction of the shoulder joint and adduction of the shoulder joint.

15. A method of treating a shoulder joint of a person using a shoulder orthosis, wherein the shoulder orthosis includes a flexion/extension device and a shoulder therapy device, the method comprising:
operatively securing at least a portion of an arm associated with shoulder joint to the shoulder orthosis;
positioning the shoulder joint, using the flexion/extension device, in one of greater than 0 degrees of flexion and greater than 0 degrees of extension, the flexion/extension device including a load bearing member and an angular positioning member having a mounting surface, wherein the load bearing member is configured to lie substantially within a sagittal plane of the person and the mounting surface is configured to angularly offset from the sagittal plane of the person when the shoulder orthosis is operatively secured to at least a portion of the arm; and operating a drive assembly of the shoulder therapy device to facilitate movement of the shoulder joint after said positioning the shoulder joint using the flexion/extension device.

16. The method set forth in claim 15, wherein said positioning the shoulder joint using the flexion/extension device comprises positioning the shoulder joint in greater than about 5 degrees of flexion.

17. The method set forth in claim 16, wherein said positioning the shoulder joint using the flexion/extension device comprises positioning the shoulder joint in greater than about 15 degrees of flexion.

18. The method set forth in claim 17, wherein said positioning the shoulder joint using the flexion/extension device comprises positioning the shoulder joint in about 30 degrees of flexion.

19. The method set forth in claim 18, further comprising positioning the shoulder joint using an abduction/adduction device in a selected degree of abduction before said operating the shoulder therapy device, wherein said operating the shoulder therapy device comprises operating an internal/external rotation device to facilitate at least one of internal rotation and external rotation of the shoulder joint.

20. A shoulder orthosis comprising:
a torso securing device configured for removable securement to a torso of a person;
an internal/external rotation device adapted to facilitate at least one of internal rotation and external rotation of a shoulder joint of the person; and
a flexion/extension device operatively connecting the internal/external rotation device to the torso securing device, the flexion/extension device including a load bearing plate arranged to lie substantially within a sagittal plane of the person when the torso securing device is secured to the torso of the person, and an angular positioning member having a mounting surface that is configured to angularly offset from the sagittal plane of the person when the torso securing device is secured to the torso of the person, wherein the flexion/extension device is configured to position the shoulder joint in greater than 0 degrees of flexion when the torso securing device is secured to the torso and as the internal/external rotation device is facilitating the at least one of internal rotation and external rotation of the shoulder joint.

21. The shoulder orthosis set forth in claim 20, wherein the flexion/extension device is configured to position the shoulder joint in greater than about 20 degrees of flexion.

22. The shoulder orthosis set forth in claim 20, wherein the flexion/extension device is configured to position the shoulder joint in about 30 degrees of flexion.

23. The shoulder orthosis set forth in claim 20, wherein the flexion/extension device is selectively adjustable to facilitate selective positioning of the shoulder joint in one of a plurality of different degrees of flexion.

24. The shoulder orthosis set forth in claim 20, further comprising an abduction/adduction device adapted to facilitate abduction of the shoulder joint.

* * * * *